US012706179B2

(12) United States Patent
Eltoukhy et al.

(10) Patent No.: US 12,706,179 B2
(45) **Date of Patent: *Aug. 11, 2026**

(54) POPULATION BASED TREATMENT RECOMMENDER USING CELL FREE DNA

(71) Applicant: GUARDANT HEALTH, INC., Palo Alto, CA (US)

(72) Inventors: Helmy Eltoukhy, Atherton, CA (US); AmirAli Talasaz, Atherton, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,388

(22) Filed: Jul. 25, 2023

(65) Prior Publication Data

US 2024/0153593 A1 May 9, 2024

Related U.S. Application Data

(63) Continuation of application No. 17/003,631, filed on Aug. 26, 2020, which is a continuation of application (Continued)

(51) Int. Cl.

*G16B 50/20* (2019.01)
*C12Q 1/6883* (2018.01)

(Continued)

(52) U.S. Cl.

CPC ........... *G16B 50/20* (2019.02); *C12Q 1/6883* (2013.01); *G16B 40/00* (2019.02); *G16B 40/20* (2019.02);

(Continued)

(58) Field of Classification Search

CPC ........ G16B 50/20; G16B 40/20; G16B 40/30; G16B 50/00; G16B 40/00; G16H 50/30;

(Continued)

(56) References Cited

U.S. PATENT DOCUMENTS

| | | | | |
|---|---|---|---|---|
| 9,109,256 | B2 | 8/2015 | Shuber | |
| 11,756,655 | B2 * | 9/2023 | Eltoukhy | G16H 20/00 703/11 |

(Continued)

FOREIGN PATENT DOCUMENTS

| | | | | |
|---|---|---|---|---|
| WO | WO-2004015608 A2 * | 2/2004 | | G06F 19/24 |
| WO | 2014151117 A1 | 9/2014 | | |

(Continued)

OTHER PUBLICATIONS

Office Action in U.S. Appl. No. 17/003,631, daed Mar. 20, 2024.

(Continued)

*Primary Examiner* — Jesse P Frumkin

(74) *Attorney, Agent, or Firm* — Stephen W. Chen

(57) ABSTRACT

Systems and methods are disclosed for generating a therapeutic response predict or detecting a disease, by: using a genetic analyzer to generate genetic information; receiving into computer memory a training dataset comprising, for each of a plurality of individuals having a disease, (1) genetic information from the individual generated at first time point and (2) treatment response of the individual to one or more therapeutic interventions determined at a second, later, time point; and implementing a machine learning algorithm using the dataset to generate at least one computer implemented classification algorithm, wherein the classification algorithm, based on genetic information from a subject, predicts therapeutic response of the subject to a therapeutic intervention.

19 Claims, 15 Drawing Sheets

Related U.S. Application Data

No. 15/766,765, filed as application No. PCT/US2016/056131 on Oct. 7, 2016, now Pat. No. 11,756,655.

(60) Provisional application No. 62/239,390, filed on Oct. 9, 2015.

(51) Int. Cl.

| | |
|---|---|
| ***C12Q 1/6886*** | (2018.01) |
| ***G16B 40/00*** | (2019.01) |
| ***G16B 40/20*** | (2019.01) |
| ***G16B 40/30*** | (2019.01) |
| ***G16B 50/00*** | (2019.01) |
| ***G16H 20/00*** | (2018.01) |
| ***G16H 50/30*** | (2018.01) |

(52) U.S. Cl.

CPC ............. *G16B 40/30* (2019.02); *G16B 50/00* (2019.02); *G16H 20/00* (2018.01); *G16H 50/30* (2018.01); *C12Q 1/6886* (2013.01)

(58) Field of Classification Search

CPC ...... G16H 20/00; G16H 50/70; C12Q 1/6883; C12Q 1/6886

See application file for complete search history.

(56) References Cited

U.S. PATENT DOCUMENTS

| | | | | |
|---|---|---|---|---|
| 2002/0029113 | A1 | 3/2002 | Wang et al. | |
| 2002/0077756 | A1 | 6/2002 | Arouh et al. | |
| 2004/0111169 | A1 | 6/2004 | Hong et al. | |
| 2005/0234570 | A1 | 10/2005 | Horsch et al. | |
| 2008/0161420 | A1 | 7/2008 | Shuber | |
| 2009/0233279 | A1 | 9/2009 | Glinskii | |
| 2010/0041048 | A1 | 2/2010 | Diehl et al. | |
| 2010/0063948 | A1 | 3/2010 | Virkar et al. | |
| 2010/0221754 | A1 | 9/2010 | Ford et al. | |
| 2011/0166030 | A1 | 7/2011 | Wang et al. | |
| 2014/0031260 | A1* | 1/2014 | O'Donnell ........... | C12Q 1/6876 506/9 |
| 2014/0296081 | A1 | 10/2014 | Diehn et al. | |
| 2015/0197785 | A1 | 7/2015 | Carter et al. | |
| 2016/0264973 | A1 | 9/2016 | Aceto et al. | |
| 2017/0073756 | A1 | 3/2017 | Jensen et al. | |
| 2017/0342500 | A1 | 11/2017 | Marquard et al. | |
| 2018/0068083 | A1 | 3/2018 | Cohen et al. | |
| 2018/0251848 | A1 | 9/2018 | Diehn et al. | |
| 2020/0131582 | A1 | 4/2020 | Zhou et al. | |
| 2020/0395100 | A1* | 12/2020 | Eltoukhy ............ | C12Q 1/6883 |
| 2021/0207223 | A1 | 7/2021 | Janne et al. | |

FOREIGN PATENT DOCUMENTS

| | | | | |
|---|---|---|---|---|
| WO | 2015058175 | A2 | 4/2015 | |
| WO | WO-2016094330 | A2 * | 6/2016 | ....... G01N 33/57423 |
| WO | 2016094330 | A3 | 7/2016 | |

OTHER PUBLICATIONS

Butler, T.M. et al. "Exome Sequencing of Cell-Free DNA from Metastatic Cancer Patients Identifies Clinically Actionable Mutations Distinct from Primary Disease" PloSOne (2015) e0136407 (14 pages).

Final Office Action for U.S. Appl. No. 17/003,631, dated Dec. 20, 2024.

Lebofsky, R. et al. "Circulating tumor DNA as a non-invasive substitute to metastasis biopsy for tumor genotyping and personalized medicine in a prospective trial across all tumor types" Mol Oncol (2014) 9(4):783-790.

Office Action for U.S. Appl. No. 17/003,631, dated Aug. 25, 2025.

* cited by examiner

FIG. 1D

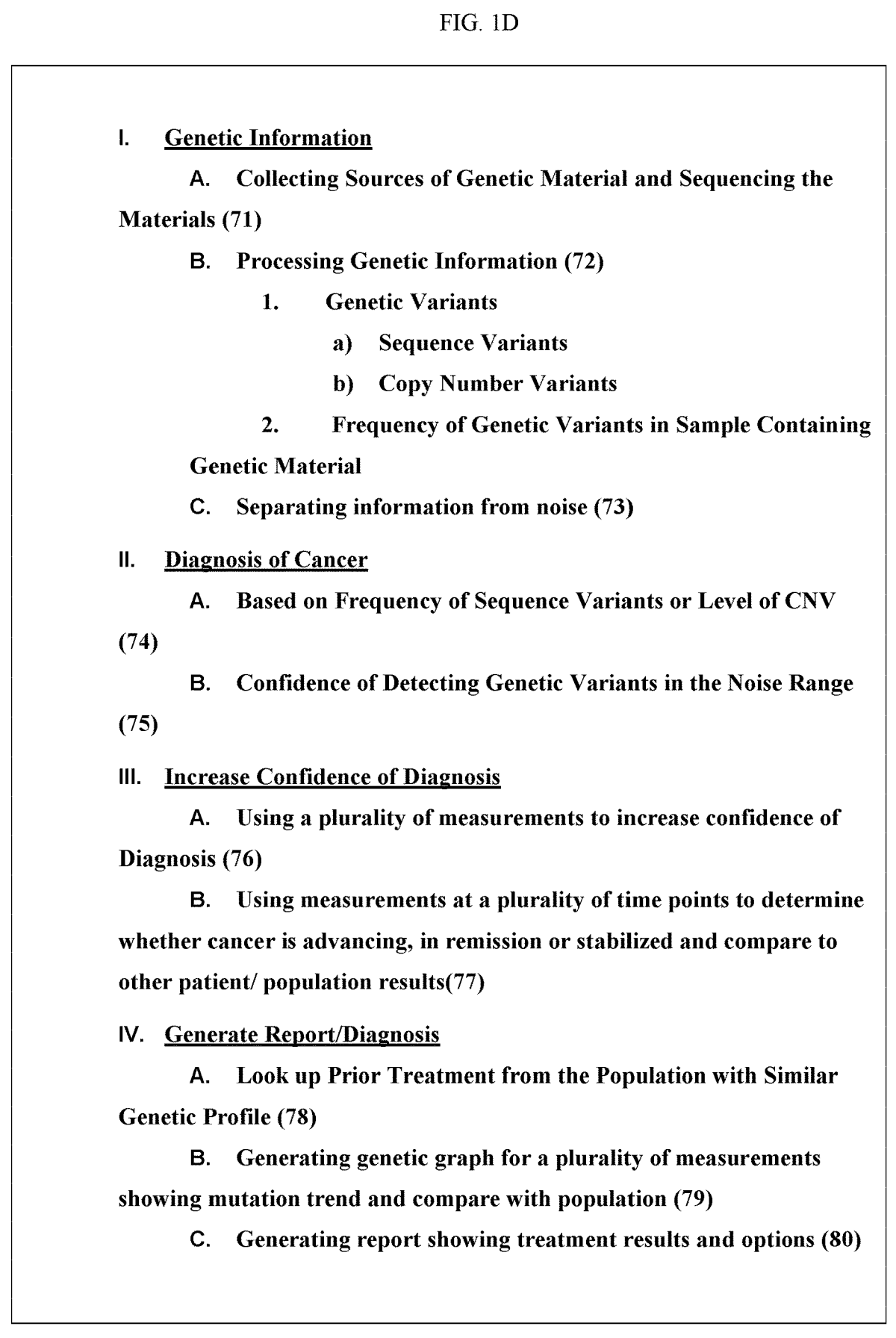

I. Genetic Information

A. Collecting Sources of Genetic Material and Sequencing the Materials (71)

B. Processing Genetic Information (72)

1. Genetic Variants a) Sequence Variants b) Copy Number Variants

2. Frequency of Genetic Variants in Sample Containing Genetic Material

C. Separating information from noise (73)

II. Diagnosis of Cancer

A. Based on Frequency of Sequence Variants or Level of CNV (74)

B. Confidence of Detecting Genetic Variants in the Noise Range (75)

III. Increase Confidence of Diagnosis

A. Using a plurality of measurements to increase confidence of Diagnosis (76)

B. Using measurements at a plurality of time points to determine whether cancer is advancing, in remission or stabilized and compare to other patient/ population results(77)

IV. Generate Report/Diagnosis

A. Look up Prior Treatment from the Population with Similar Genetic Profile (78)

B. Generating genetic graph for a plurality of measurements showing mutation trend and compare with population (79)

C. Generating report showing treatment results and options (80)

FIG. 2B

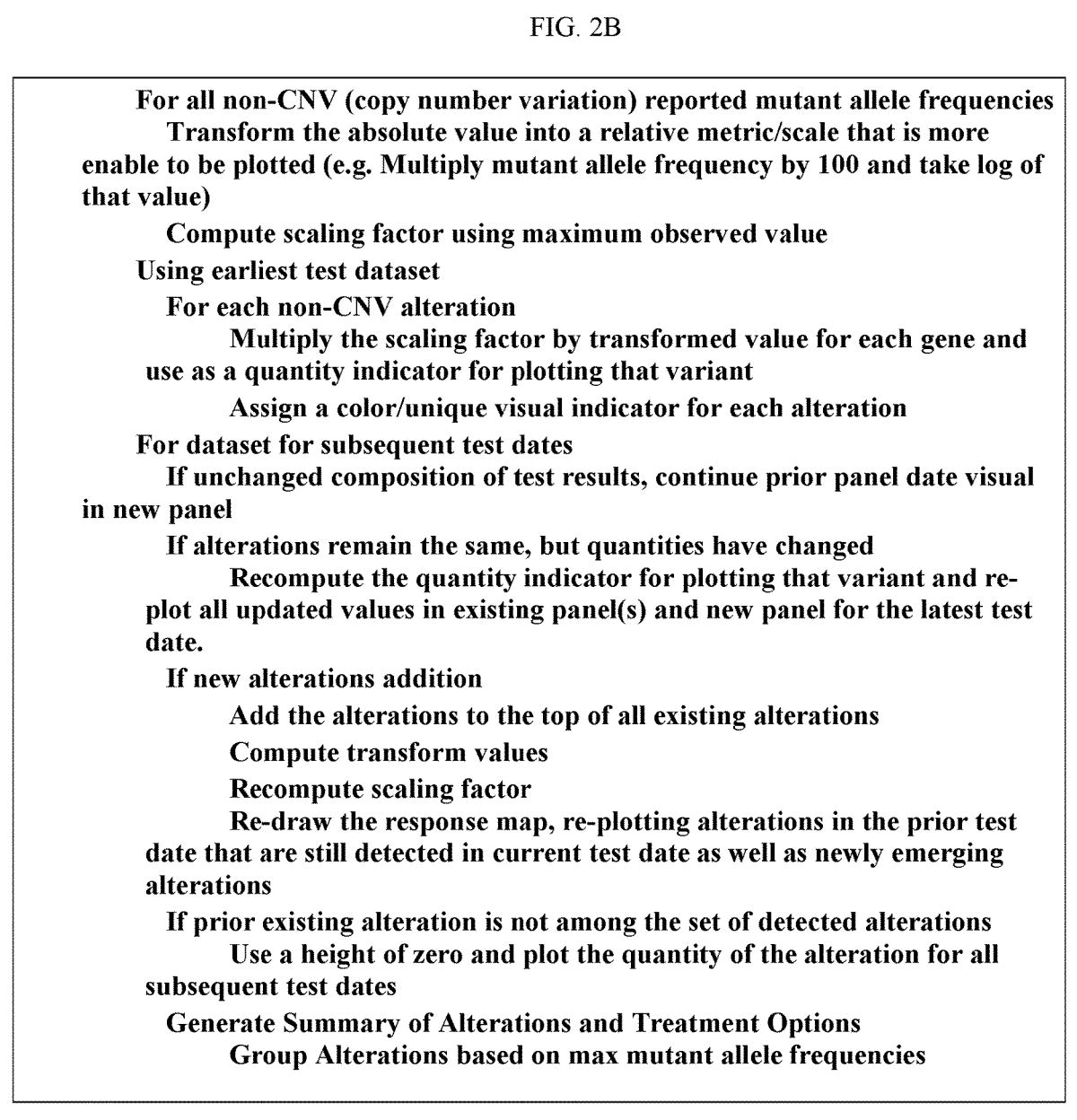

For all non-CNV (copy number variation) reported mutant allele frequencies
Transform the absolute value into a relative metric/scale that is more enable to be plotted (e.g. Multiply mutant allele frequency by 100 and take log of that value)
Compute scaling factor using maximum observed value
Using earliest test dataset
For each non-CNV alteration
Multiply the scaling factor by transformed value for each gene and use as a quantity indicator for plotting that variant
Assign a color/unique visual indicator for each alteration
For dataset for subsequent test dates
If unchanged composition of test results, continue prior panel date visual in new panel
If alterations remain the same, but quantities have changed
Recompute the quantity indicator for plotting that variant and re-plot all updated values in existing panel(s) and new panel for the latest test date.
If new alterations addition
Add the alterations to the top of all existing alterations
Compute transform values
Recompute scaling factor
Re-draw the response map, re-plotting alterations in the prior test date that are still detected in current test date as well as newly emerging alterations
If prior existing alteration is not among the set of detected alterations
Use a height of zero and plot the quantity of the alteration for all subsequent test dates
Generate Summary of Alterations and Treatment Options
Group Alterations based on max mutant allele frequencies

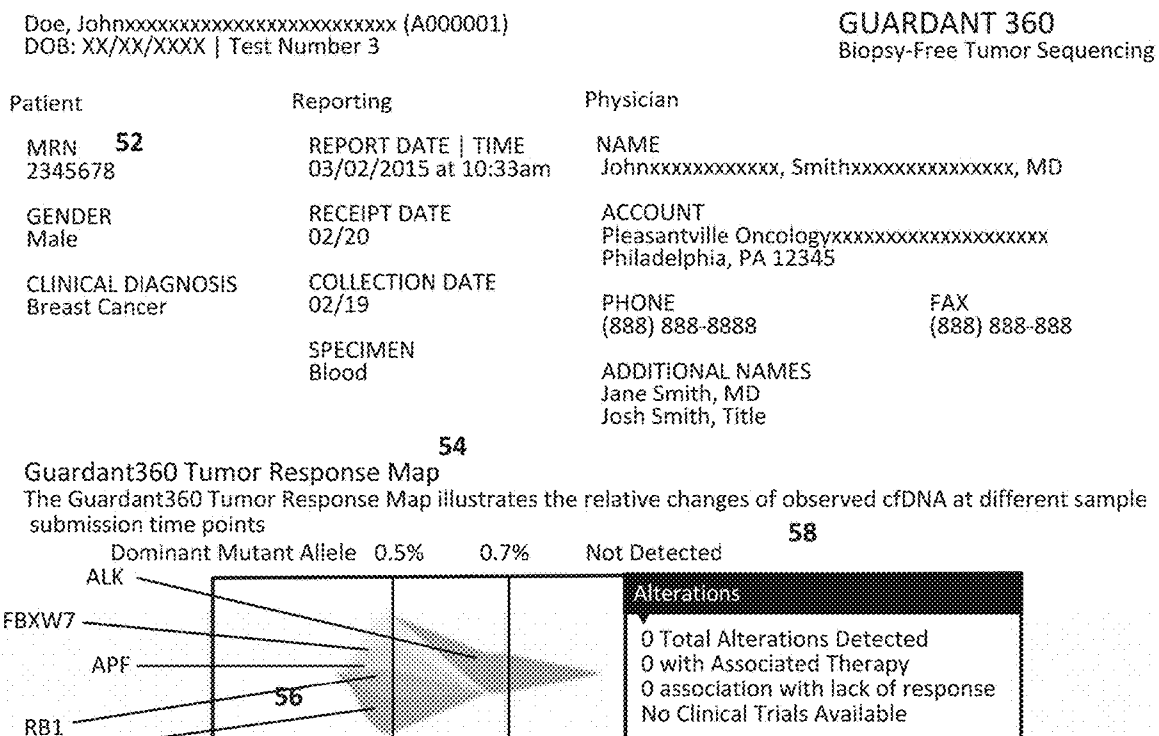

NOTE: Genomic alterations may be present that are below the limit of detection of this test. Certain sample or variant characteristics may result in reduced analytic sensitivity, such as poor sample quality or improper collection. Genomic alternations in a tumor may be present, but are not detected in circulating cell-free DNA from this blood specimen with this test.

Summary of Alterations & Associated Treatment Options 60

The percentage of genomic alterations found in cell free DNA circulating in blood is related to the unique tumor biology of this patient. Factors that may affect the amount/percentages of detected genomic alterations in circulating cell free DNA in blood include tumor growth, turn over, size, heterogeneity, vascularization, disease progression, or treatment.

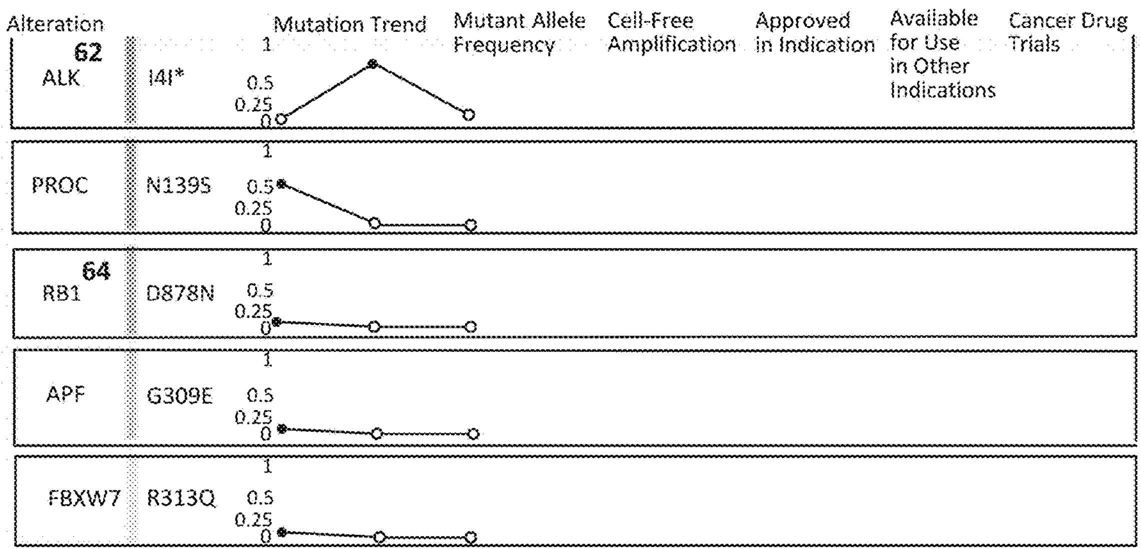

Figure 2C

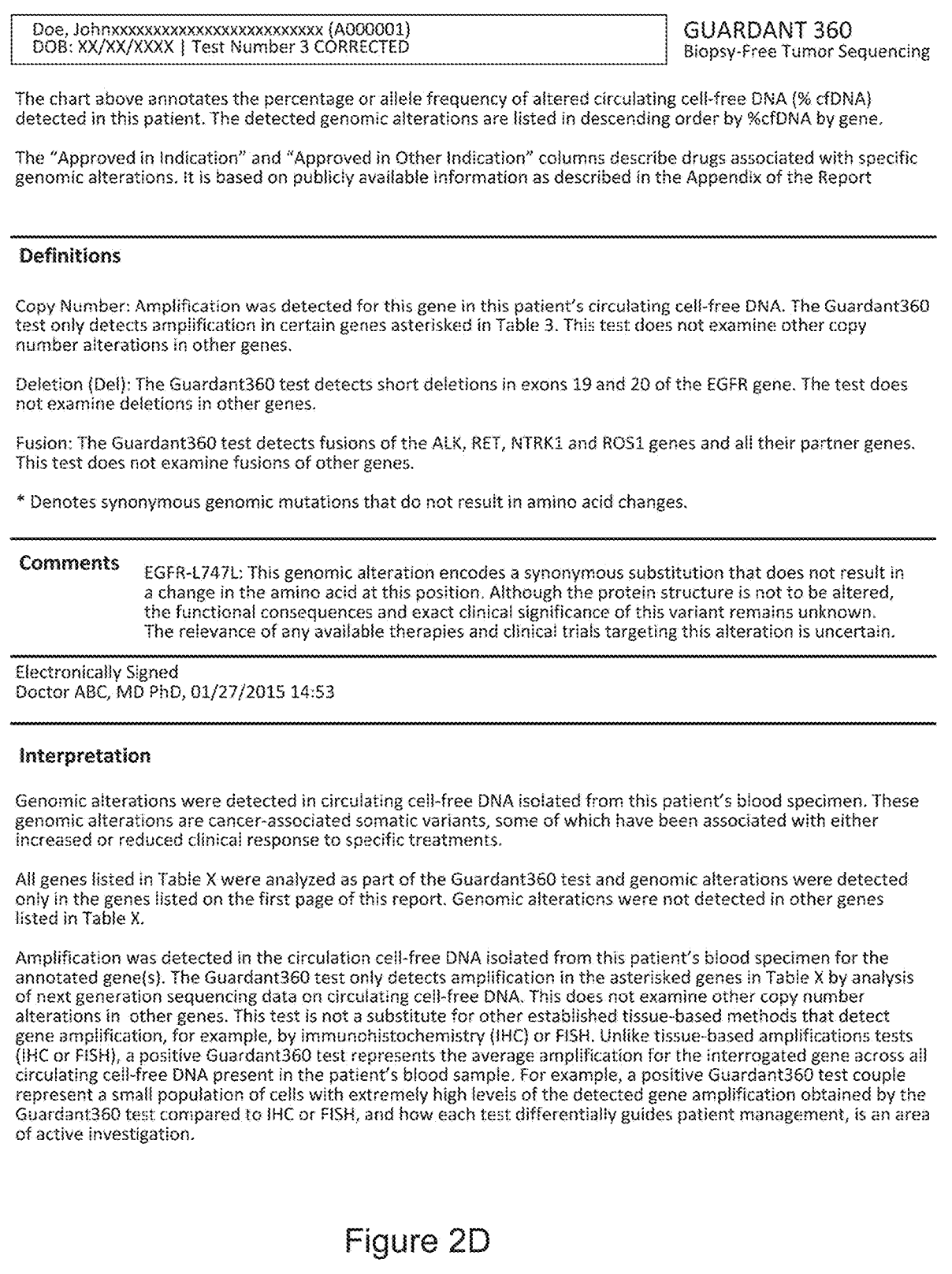

| Doe, Johnxxxxxxxxxxxxxxxxxxxxxxxxxx (A000001)<br>DOB: XX/XX/XXXX \| Test Number 3 CORRECTED | GUARDANT 360<br>Biopsy-Free Tumor Sequencing |
|---|---|

The chart above annotates the percentage or allele frequency of altered circulating cell-free DNA (% cfDNA) detected in this patient. The detected genomic alterations are listed in descending order by %cfDNA by gene.

The "Approved in Indication" and "Approved in Other Indication" columns describe drugs associated with specific genomic alterations. It is based on publicly available information as described in the Appendix of the Report

Definitions

Copy Number: Amplification was detected for this gene in this patient's circulating cell-free DNA. The Guardant360 test only detects amplification in certain genes asterisked in Table 3. This test does not examine other copy number alterations in other genes.

Deletion (Del): The Guardant360 test detects short deletions in exons 19 and 20 of the EGFR gene. The test does not examine deletions in other genes.

Fusion: The Guardant360 test detects fusions of the ALK, RET, NTRK1 and ROS1 genes and all their partner genes. This test does not examine fusions of other genes.

* Denotes synonymous genomic mutations that do not result in amino acid changes.

Comments

EGFR-L747L: This genomic alteration encodes a synonymous substitution that does not result in a change in the amino acid at this position. Although the protein structure is not to be altered, the functional consequences and exact clinical significance of this variant remains unknown. The relevance of any available therapies and clinical trials targeting this alteration is uncertain.

Electronically Signed
Doctor ABC, MD PhD, 01/27/2015 14:53

Interpretation

Genomic alterations were detected in circulating cell-free DNA isolated from this patient's blood specimen. These genomic alterations are cancer-associated somatic variants, some of which have been associated with either increased or reduced clinical response to specific treatments.

All genes listed in Table X were analyzed as part of the Guardant360 test and genomic alterations were detected only in the genes listed on the first page of this report. Genomic alterations were not detected in other genes listed in Table X.

Amplification was detected in the circulation cell-free DNA isolated from this patient's blood specimen for the annotated gene(s). The Guardant360 test only detects amplification in the asterisked genes in Table X by analysis of next generation sequencing data on circulating cell-free DNA. This does not examine other copy number alterations in other genes. This test is not a substitute for other established tissue-based methods that detect gene amplification, for example, by immunohistochemistry (IHC) or FISH. Unlike tissue-based amplifications tests (IHC or FISH), a positive Guardant360 test represents the average amplification for the interrogated gene across all circulating cell-free DNA present in the patient's blood sample. For example, a positive Guardant360 test couple represent a small population of cells with extremely high levels of the detected gene amplification obtained by the Guardant360 test compared to IHC or FISH, and how each test differentially guides patient management, is an area of active investigation.

Figure 2D

Doe, Johnxxxxxxxxxxxxxxxxxxxxxxxxxxx (A000001)
DOB: XX/XX/XXXX | Test Number 3 | Status: CORRECTED GUARDANT 360
Biopsy-Free Tumor Sequencing

Detailed Therapy Results

| Alteration | Drug | Trade Name | Target | Current Status |
|---|---|---|---|---|
| EGFR T790M amplification | Neratrib | | Egfr/Her2/ErbB4 inhibitor | Phase 2 (Non-small cell lung carcinoma (NSCLC)) Phase 3 (Breast carcinoma) |
| | CO-1686 | | Egfr T790M Inhibitor | Phase 2 (Non-small cell lung carcinoma (NSCLC)) Phase 2 (Lung cancer) |
| | Panitumumab | Vectibix | Egfr Inhibitory antibody | Phase 2 (Non-small cell lung carcinoma (NSCLC)) FDA approved in other indications (Colorectal carcinoma) |
| | AZD9291 | | Egfr T790M Inhibitor | Phase 3 (Non-small cell lung carcinoma (NSCLC)) Phase 3 (Lung cancer) |
| | Afatinib | Gilotrif | Irreversible pan-erb Bkinase inhibitor | FDA Approved in this indication (Non-small cell lung carcinoma (NSCLC)) FDA Approved in other indications (Lung cancer) |
| | Lapatinib | Tykerb | Egfr Inhibitory antibody | Phase 2 (Non-small cell lung carcinoma (NSCLC)) FDA approved in other indications (Breast carcinoma) |
| | Dacomitinib | | Egfr T790M Inhibitor | Phase 3 (Non-small cell lung carcinoma (NSCLC)) Phase 3 (Lung cancer) |
| | Nimotuzumab | Theraloc | Egfr Inhibitory antibody | Phase 2 (Non-small cell lung carcinoma (NSCLC)) Phase 3 (Gastric carcinoma, Adeno carcinoma of the nasopharynx), Glioblastoma, Head and neck squamous cell carcinoma (JNSCC), Gastroesophageal junction carcinoma, Esophageal carcinoma, Squamous cell carcinoma of the tongue |
| | Cetuximab | Erbitux | Egfr Inhibitory antibody | Phase 3 (Non-small cell lung carcinoma (NSCLC)) FDA Approved in other indications Head and neck squamous cell carcinoma (HNSCC),Squamous cell carcinoma of the tongue, Colorectal carcinoma |
| MET amplification | Crizotinib | Xalkori | ALK/Met Kinase Inhibitor | FDA Approved in other indications (Non-small cell lung carcinoma (NSCLC)) Phase 2 (Gastric carcinoma, Renal cell carcinoma) |
| | LY280166β | | Multi-kinase inhibitor targeting Met, Ros1, Axl, FitB and other proteins | Phase 1 (Solid Tumor) |
| | BMS-777607 | | Met/Ret/VEGFR 1,2,3/Kit/ FitB/Tie2/TrkB/Axl small molecule kinase inhibitor | Phase 2 (Gastric carcinoma, Prostate Carcinoma, Renal cell carcinoma, Head and neck squamous cell carcinoma (HNSCC),Cutaneous squamous cell carcinoma, Esophageal carcinoma |
| | Cabozantinib | Cometriq | Met/Ret/VEGFR 1,2,3/Kit/ FitB/Tie2/TrkB/Axl small molecule kinase inhibitor | Phase 2 (Non-small cell lung carcinoma (NSCLC)) FDA approved in other indications (Thyroid medullary carcinoma) |
| | Foretinib | | Met/VEGFR2 small molecule kinase inhibitor | Phase 2 (Non-small cell lung carcinoma (NSCLC)), Phase 2 (Gastric carcinoma, Hepatocellular carcinoma, Renal cell carcinoma, Head and neck squamous cell carcinoma |

Continued on next page

Figure 2E

Doe, Johnxxxxxxxxxxxxxxxxxxxxxxxxxx (A000001)
DOB: XX/XX/XXXX | Test Number 3|Status: CORRECTED GUARDANT 360
Biopsy-Free Tumor Sequencing

Clinical Relevance of Detected Alterations

| Alteration | Role in Disease | Effect on Drug Sensitivity | Effect on Drug Resistance |
|---|---|---|---|
| EGFR T790M amplification | | 18784101, Van Cutsem et al., 2007; 17470868. Based on accumulated evidence, the American Society for Clinical Oncology (ASCO) has issued a Provisional Clinical Opinion recommending EGFR mutational analysis for NSCLC patients to predict benefit from Efgr TKIs (Keedy et al., 2011:21482992) | |
| MET amplification | Met protein activation or overexpression promotes angiogenesis, resistance to apoptosis, proliferation, and invasion of cancel cells (Appleman, 2011; 22042966, Jung et al., 2012;22660361, Gherardi et al., 2012;2270963, Takeuchi et al., 2008;12684423). Met protein expression in NSCLC has been associated with a predisposition to the development of brain metastases (Benedettini et al., 2010;20489160). | Increased Met expression, possibly as a result of MET mutation or amplification, may lead to enhanced Met activation and may therefore confer sensitivity to Met inhibitors (Cecchi et al., 2010:20303741). Crizotinib and Cabozantinib target multiple kinases including Met. Crizotinib has been FDA approved for use in EML4-ALK positive non small cell lung cancer, and cabozanitnib has been FDA approved for medullary thyroid cancer (Carridge et al., 2011; ASCO 2011, Abstract 2601, Bang et al.< 2010 ASCO 2010, Abstract B, Traynor, 2013;23292267, Hart and DeBoer, 2013;23319867). Reports in multiple tumor types suggest that met amplification may predict sensitivity to critzotinib (Lennerz et al., 2011;22042947, Chi et al., 2012;22162673, Ou et al., 2011;21623266). Met specific inhibitors are in clinical development including Tivantinib (ARQ 197) a selective non-ATP competitive met inhibitor and a monoclonal antibody targeting Met (Adjel et al., 2011;21632449, Bendell et al., 2013; 23810377, Eng et al., 2013; ASCO 2013, Abstract 3608). | Met amplification elevated Met expression has been implicated in acquired resistance to Egfr inhibitors in some cancer types; studies are currently investigating combination therapy with Met inhibitors and Egfr inhibitors in this setting (Krumbach et al., 2011;21273060, Engelman et al., 2007;17463260, Chen et al., 2013, 2327267). Met activation has been implicated as one key mechanism of resistance of Egfr-targeted therapy in NSCLC (Engelman et al., 2007;17463260, La et al., 2013;24167634, Benedettini et al., |
| NOTCH1 P24386 | Depending on cellular context, NOTCH1 can act as either a tumor suppressor or oncogene (Wang et al., 2011;22006338, Kilnakis et al., 2011;21662664). Notch1 activity has been reported to be required for lung tumorgenesis in K-Ras driven NSCLC models, and has been linked to a stem cell phenotype (Licciulli et al. 2013;23943799, Baumgart et al., 2014;24609876, Hassan et al., 2013;23444212, Allen et al., 2011;21803744). | Activating NOTCH1 mutations stabilize the Notch1 intracellular protein and lead to increased Notch1 signaling (Weng et al., 2004;14672076). Notch1 inhibitors (i.e., gamma-secretase inhibitors, which prevent cleavage of the intracellular domain) may be a potential therapeutic approach in the case of NOTCH1 activating mutations, and these are in clinical trials for various cancers (Fouladi et al., 2011;21826264, Groth and Fontini, 2012;22309842). Gamma-secretase inhibitors have shown efficacy in preclinical tumor models with Notch activation (Westhoff et al., 2009;20007776, Arcaroll et al., 2013;23868008). Some studies suggest that HDAC inhibitors include LBH689 and valproic acid, may reactivate Notch pathway signaling in some tumors that have lost Notch expression (Egloff and Grandis, 2012;22773620, Platta et al., 2008,18670928). However, this approach is relevant in the context of epigenetic silencing and is not expected to be relevant in the case of NOTCH1 inactivating mutation. In the case of the uncharacterized variant, the relevance of any available therapeutic approaches in unknown. | In a preclinical study using NSCLC cell lines and xenografts, Notch1 has been suggested to play a role in acquired resistance to Egfr tyrosine kinase inhibitors such as gelitirib (Xie et al., 2013;23916913, Xie et al., 2013;22173964). In addition, NSCLC cell lines with high, or activated, Notch1 have been reported to be resistant to chemotherapies, including cisplatin and docetaxel (Hassan et al., 2013;23444212, Liu et al., 2013;23136908). |

Figure 2F

Doe, Johnxxxxxxxxxxxxxxxxxxxxxxxxxxx (A000001)
DOB: XX/XX/XXXX | Test Number 3|Status: CORRECTED GUARDANT 360
Biopsy-Free Tumor Sequencing

Available Clinical Trials

| Alteration | Trial ID | Title | Phase | Site |
|---|---|---|---|---|
| EGFR T790M amplification | NCTO647711 | A study of intermittent, High-dose Afatinib to Determine the Maximal Tolerated Dose and Assess Activity of This Dose Against Non-small Cell Lung Cancer with T790M Mutations | Phase 1 | Aurora, CO<br>Boston, MA (2) |
| | NCTO1626928 | Study to Evaluate Safety, Pharmacokinetics, and Efficacy of Rociletinib (CO-1686) in Previously Treated Mutant Epidermal Growth Factor Recap for (EGFR) in Non-Small Cell Lung Cancer (NSCLC) Patients | Phase 1/Phase 2 | Duarte, CA; Fountain Valley, CA; Los Angeles, CA (2); Orange, CA; Stanford, CA; Whittier, CA (2); Aurora, CA; Washington, DC; Miami, FL; Orlando, FL; Athens, Ga; Boston, MA(2); Ann Arbor, MI; Detroit, MI; Morristown, NJ; Buffalo, NY; Lake Success, NY: New York, NY; Cincinnati, OH; Columbus, OH; Tulsa, OK; Portland, OR; Philadelphia, PA; Pittsburgh, PA; Nashville, TN; Houston, TX |
| MET amplification | NCTO1324479 | Study of NC280 in Patients With c-MET Dependent Advanced Solid Tumors | Phase 1 | Fayetteville, AK; Los Angeles, CA; Chicago, IL; Rockville, MD; Detroit, MI; Buffalo, NY; Nashville, TN; Dallas, TX; Houston, TX; Salt Lake City, UT; Australia (2); Canada (2); France (3); Germany (6); Hong Kong (2); Israel (4); Italy (6); Korea (6); Netherlands (3); Norway; Singapore; Granada, Spain (6); Taiwan (2); Thailand (3) |
| | NCTO1712217 | Study of At13387 in Patients With Non-Small Cell Lung Cancer (NSCLC) Alone and in Combination with Crizotinib | Phase 1/Phase 2 | Scottsdale, AZ; LaJolla, CA; Los Angeles, CA; San Diego, CA; Santa Monica, CA; Whittier, CA; Aurora, CA; New Haven, CT; Newark, DE; Orlando, FL; Tampa, FL; Chicago, IL (2); Ann Arbor, MI; Detroit, MI; Rochester, MN; St. Louis, MO; Omaha, NE; Lebanon, NH; Bronx, NY; New York, NY; Greensboro, NC; Winston Salem, NC; Cincinnati, OH (2); Cleveland, OH; Columbus, OH; Portland, OR; Hershey, PA; Philadelphia, PA; Memphis, TN; Nashville, TN; Dallas, TX; Fairfax, VA; Seattle, WA (2); Madison, WI; Canada (6); France (10); Korea (6); Spain (6) |

Figure 2G

Doe, Johnxxxxxxxxxxxxxxxxxxxxxxxxxxx (A000001)
DOB: XX/XX/XXXX | Test Number 3|Status: CORRECTED GUARDANT 360
Biopsy-Free Tumor Sequencing

Methods and Limitations

Guardant 260 assays a panel of 68 genes to identify genomic alterations in cancer-associated somatic variants with high sensitivity. Cell-free DNA is extracted from plasma and genomic alterations are analyzed by massively parallel sequencing of amplified target genes. For one set of genes, all exons are sequenced as such sequencing coverage has shown to have clinical utility. For another set of genes, sequencing coverage includes those exons with a previously reported somatic mutation. Synonymous substitutions are reported if present, although the exact clinical significance and relevance of any available therapies targeting such variants are not precisely defined. The minimum detectable mutant allele (limit of detection) is dependent on the patient's sample cell-free DNA concentration, which can vary from less than 10 to over 1000 genomic equivalents per mL of peripheral blood. The Guardant360 test is validated to only detect gene amplifications in the asterisked genes in Table X in samples with at least @% tumor derived circulating cell-free DNA that contains 8-10x gene amplification; amplification may not be detected in sample with lower amounts of cell-free DNA and/or low-level gene copy amplification. The types of genomic alterations that can be detected by HARdant360 include single nucleotide variations, amplifications, ALK, NTRK1, RET and ROS1, fusions, and short insertions/deletions present in exons 19 and 20 of the EGFR gene. The version of the Guardant360 test is not validated for the detection of other types of genomic alterations (for example gene deletions, frameshifts, splice variants or indels). Certain sample or variant characteristics may result in reduced analytic sensitivity, such as low sample quality or improper collection.

Table X annotates the patient specific limit of detection (LOD) for each of the genes analyzed, which is dependent on cell-free DNA concentration and sequencing coverage for that gene.

Genes on the Guardant360 Panel and Associated LOD

Genes with Complete Exon and Partial Intron Coverage

| Gene | LOD | Gene | LOD | Gene | LOD | Gene | LOD |
|---|---|---|---|---|---|---|---|
| APC | 0.1% | AR | 0.2% | ARID1A | 0.2% | BRAF | 0.1% |
| BRCA1 | 0.2% | BRCA2 | 0.2% | CCND1 | 0.1% | CCND2 | 0.1% |
| CCNe1 | 0.1% | CDK4 | 0.1% | CDK6 | 0.2% | CDKN2A | 0.1% |
| CDKN2B | 0.1% | EGFR*+ | 0.1% | ERBB2 | <0.1% | FGFR1 | 0.1% |
| FGFR2 | 0.1% | HRAS | 0.1% | KIT | 0.1% | KRAS | 0.1% |
| MET | 0.1% | MYC | <0.1% | NF1 | 0.2% | NRAS | 0.2% |
| PDGFRA | 0.1% | PIK5CA | 0.2% | PTEN | 0.2% | RAF1 | 0.2% |
| TP63 | 0.2% | | | | | | 0.1% |

Genes in bold are those that are also analyzed for copy number variations (CNVs)
*EGFR indels in exons 19 and 20

Genes with Critical Exon Coverage

| Gene | LOD | Gene | LOD | Gene | LOD | Gene | LOD |
|---|---|---|---|---|---|---|---|
| AKT1 | <0.1% | ALK | 0.1% | ARAF | 0.2% | ATM | 0.2% |
| CDH1 | 0.2% | CTNNB1 | <0.1% | ESRY | 0.1% | EZH2 | 0.1% |
| FBKW7 | 0.1% | FGFR3 | 0.1% | GATA3 | 0.1% | GNA11 | 0.1% |
| GNAQ | 0.1% | GNAS | 0.1% | HNF1A | 0.1% | IDH1 | 0.1% |
| IDH2 | 0.1% | JAK2 | 0.2% | JAK3 | 0.1% | MAPK1 | 0.1% |
| MAP2K2 | 0.1% | MLH1 | 0.2% | MPL | 0.1% | NFE2L2 | 0.1% |
| NOTCH1 | 0.1% | NPMY | 0.2% | NTRKY | <0.1% | PTPN11 | 0.1% |
| RET | <0.1% | RHEB | 0.2% | RHOA | 0.1% | RIT1 | 0.1% |
| ROS1 | 0.2% | SMAD4 | 0.2% | SMO | 0.1% | SRC | <0.1% |
| STK1 | 0.1% | TERT^ | 0.1% | VHL | 0.2% | | |

^Includes promoter region

Rearrangements

| Gene | LOD | Gene | LOD | Gene | LOD | Gene | LOD |
|---|---|---|---|---|---|---|---|
| ALK | <0.1% | NTRKY | <0.1% | RET | <0.1% | ROS1 | <0.2% |

Figure 2H

POPULATION BASED TREATMENT RECOMMENDER USING CELL FREE DNA

CROSS-REFERENCE

This application is a continuation application of U.S. patent application Ser. No. 17/003,631, filed Aug. 26, 2020, which is a continuation application of U.S. patent application Ser. No. 15/766,765, filed Apr. 6, 2018, which is a national stage application of PCT application No. PCT/US2016/056131, filed Oct. 7, 2016, which claims the benefit of U.S. Provisional Application No. 62/239,390, filed Oct. 9, 2015, which applications are incorporated herein by reference in its entirety.

BACKGROUND

Individual patients respond to medical treatment differently, which is due, in part, to genetic and epigenetic differences that affect gene expression. These differences may be present in the normal host tissue, or they may be acquired by cancer cells during transformation. Such differences may affect diverse components of treatment response, including: a drug's pharmacokinetics (e.g., metabolism or transport) or pharmacodynamics (e.g., a target or modulating enzyme); host tissue sensitivity to radiation; the sensitivity of malignant cells to cytotoxic agents, including drugs and radiation; and the ability of malignant cells to invade and metastasize.

One of the reasons cancer is so difficult to treat is that current testing methods often do not help doctors match specific cancers with effective drug treatments. Moreover, the disease state itself can be a moving target—cancer cells are constantly changing and mutating. Although cancer tumors continually shed their unique genomic material into the bloodstream, unfortunately, these telltale genomic "signals" are so weak that current genomic analysis technologies, including next-generation sequencing, can only detect such signals sporadically or in patients with terminally high tumor burden. The main reason for this is that such technologies are plagued by error rates and bias that can be orders of magnitude higher than what is required to reliably detect de novo genomic alterations associated with cancer. Thus, improved systems and methods for determining effective treatments for cancer are needed.

SUMMARY OF THE INVENTION

The present invention relates to systems and methods for classifying cancer patients based on a predicted therapeutic response.

In one aspect, the present disclosure provides a method for analyzing a disease state of a subject by characterizing the subject's genetic information at two or more time points with a genetic analyzer, e.g., a DNA sequencer; and using the information from the two or more people or time points to produce an adjusted test result in the characterization of the subject's genetic information.

In another aspect, systems and methods are disclosed for detecting a disease by using a DNA sequencer to generate genetic information; receiving into computer memory a training dataset comprising, for each of a plurality of individuals having a disease, (1) genetic information from the individual generated at first time point and (2) treatment response of the individual to one or more therapeutic interventions determined at a second, later, time point; and implementing a machine learning algorithm using the dataset to generate at least one computer implemented classification algorithm, wherein the classification algorithm, based on genetic information from a subject, predicts therapeutic response of the subject to a therapeutic intervention. As used herein, a therapeutic response is a treatment response to a particular therapeutic intervention.

In another aspect, a method detects a trend in the amount of cancer polynucleotides in a sample from a subject over time by determining a frequency of the cancer polynucleotides at a plurality of time points; determining an error range for the frequency at each of the plurality of time points; determining, between an earlier and later time point, whether error ranges (1) overlap, indicating stability of frequency, (2) an increase at the later time point outside the error range, indicating increase in frequency or (3) a decrease at the later time point outside the error range, indicating decrease in frequency.

In yet another aspect, a method detects abnormal cellular activities by sequencing of cell-free nucleic acid with a genetic analyzer, e.g., a DNA sequencer; comparing later (e.g., current) sequence reads with prior sequence reads from at least two time points and updating a diagnostic confidence indication accordingly; and detecting the presence or absence of genetic alteration and/or amount of genetic variation in an individual based on the diagnostic confidence indication of the sequence read. A genetic analyzer includes any system for genetic analysis, e.g., by sequencing (DNA sequencer) or hybridization (microarray, fluorescent in situ hybridization, bionanogenomics) or other.

In another aspect, a method detects a mutation in a cell-free or substantially cell free sample obtained from a subject by generating consensus sequences by comparing later (e.g., current) sequence reads by a genetic analyzer, e.g., a DNA sequencer, with prior sequence reads from a prior period and updating a diagnostic confidence indication based on the prior sequence reads, each consensus sequence corresponding to a unique polynucleotide among a set of tagged parent polynucleotides, and generating a genetic profile of extracellular polynucleotides in the subject, wherein the genetic profile comprises a plurality of data resulting from copy number variation or mutation analyses.

In another aspect disclosed herein is a method to detect abnormal cellular activities by providing at least one set of tagged parent polynucleotides, and for each set of tagged parent polynucleotides; amplifying the tagged parent polynucleotides in the set to produce a corresponding set of amplified progeny polynucleotides; with a genetic analyzer, e.g., a DNA sequencer, sequencing a subset of the set of amplified progeny polynucleotides, to produce a set of sequencing reads; and collapsing the set of sequencing reads to generate a set of consensus sequences by comparing current sequence reads with prior sequence reads from at least one prior period and updating diagnostic confidence indication accordingly, each consensus sequence corresponding to a unique polynucleotide among the set of tagged parent polynucleotides.

In yet another aspect, a method detects a mutation in a cell-free or substantially cell free sample obtained from a subject by sequencing extracellular polynucleotides from a bodily sample from a subject with a genetic analyzer, e.g., a DNA sequencer; for each of the extracellular polynucleotide, generating a plurality of sequencing reads; filtering out reads that fail to meet a set threshold; mapping sequence reads derived from the sequencing onto a reference sequence; identifying a subset of mapped sequence reads that align with a variant of the reference sequence at each mappable base position; for each mappable base position, calculating a ratio of (a) a number of mapped sequence reads that include a variant as compared to the reference sequence, to (b) a number of total sequence reads for each mappable base position; and comparing current sequence reads with prior sequence reads from at least on other time point and updating a diagnostic confidence indication accordingly.

In a further aspect disclosed herein is a method of characterizing the heterogeneity of an abnormal condition in a subject by comparing later (e.g., current) sequence reads with prior sequence reads from at least one other time point and updating a diagnostic confidence indication accordingly, each consensus sequence corresponding to a unique polynucleotide among the set of tagged parent polynucleotides, and generating a genetic profile of extracellular polynucleotides in the subject, wherein the genetic profile comprises a plurality of data resulting from copy number variation or mutation analyses.

Implementations of the above system/method can include one or more of the following. The method includes generating a genetic profile of extracellular polynucleotides in the subject, wherein the genetic profile comprises a plurality of data resulting from copy number variation or mutation analyses. The method includes increasing a diagnostic confidence indication in the subsequent characterization if the information from a first time point corroborates information from the second time point. A diagnostic confidence indication can be increased in the subsequent characterization if the information from a first time point corroborates information from the second time point. The method includes decreasing a diagnostic confidence indication in the subsequent characterization if the information from a first time point conflicts with information from the second time point.

Advantages of the above system may include one or more of the following. Tumor-derived copy number aberrations, single nucleotide variations and methylation changes can be detected using the instant and the information can be applied to a population to increase accuracy. Also, the system can identify successful treatment for genetically similar cases, including the analysis of therapeutic targets and drug resistance—conferring gene mutations on circulating tumor cells (CTCs) and cell-free circulating tumor DNA (ctDNA) released into the peripheral blood. Both CTCs and ctDNA provide complementary information on assessing new drugs or drug combinations on the population. The liquid biopsy concept will contribute to a better understanding and clinical management of drug resistance in patients with cancer. The enumeration and characterization of circulating tumor cells (CTCs) in the peripheral blood may provide important prognostic information and might help to monitor efficacy of therapy. Since current assays cannot distinguish between apoptotic and viable CTCs, the fluoroEPISPOT assay that detects proteins secreted/released/shed from single epithelial cancer cells can be used for breast, colon, prostate, head & neck and ovarian cancer as well in melanoma. The system enables a whole range of high throughput technologies (e.g. planar- and bead microarrays, microfluidic quantitative PCR, Luminex bead technology) to meet the special demands and challenges of diagnostic biomarker discovery—and validation in body fluids. Autoantibody- and DNA methylation-based diagnostic marker panels for the big 4 cancer entities (breast, colon, prostate, lung) can be done in serum or plasma. The system can work with blood, urine or saliva as a diagnostic matrix. The genomic analysis technology architecture reduces the noise and distortion generated by next-generation sequencing to almost zero. Digital Sequencing enables ultra high-fidelity, single-molecule detection of actionable tumor-specific genomic alterations in cancer with unparalleled specificity and breadth. Put another way, clinicians can now non-invasively see the genomic dimension of cancer throughout a patient. The system comprehensively detects resistance and sensitivity mutations outside of a tumor biopsy. A simple blood draw tests a number of genes including SNVs, CNVs, indels, and rearrangements across a large number of base pairs, aiding in treatment management. The system also allows the genomic dimensions of cancer to be used to guide treatment regimens for the patient. Correlations between drug treatment efficacy and the presence or absence of molecular markers in a patient sample can be used to improve treatment. The resulting recommendation and the clinical reports are intuitive to comprehend and requires a basic level of sophistication with the testing process and familiarity with the scientific terminology used to describe the test result. This is done without requiring additional educational materials that explain the indications for testing and the interpretation of the test results. The laboratory report focuses on the important information to help the treating professional's ability to understand and correctly apply the information in clinical practice. The reports facilitate correct interpretation of complex DNA test information. The improved communication of genetic test results leads to a reduction in the misinterpretation of genetic test results, and improves the delivery of interventions or treatments based on the DNA sequencing results.

In one aspect, the present disclosure provides a method for generating a therapeutic response predictor, comprising: using a genetic analyzer to generate genetic information; receiving into computer memory a training dataset comprising, for each of a plurality of individuals having a disease, (1) genetic information from the individual generated at first time point and (2) treatment response of the individual to one or more therapeutic interventions determined at a second, later, time point; and implementing a machine learning algorithm using the dataset to generate at least one computer implemented classification algorithm, wherein the classification algorithm, based on genetic information from a subject, predicts therapeutic response of the subject.

In some embodiments, the machine learning algorithm is selected from the group consisting of: a supervised or unsupervised learning algorithm selected from support vector machine, random forest, nearest neighbor analysis, linear regression, binary decision tree, discriminant analyses, logistic classifier, and cluster analysis. In some embodiments, the method comprises predicting a direction of tumor development based on tests at two or more time points. In some embodiments, the generated prediction comprises determining a probability of developing distant metastases. In some embodiments, the training dataset further comprises clinical data selected from the group consisting of cancer stage, type of surgical procedure, age, tumor grading, depth of tumor infiltration, occurrence of post-operative complications, and the presence of venous invasion. In some embodiments, the genetic information comprises variables defining the genomic organization of cancer cells. In some embodiments, the genetic information comprise variables defining the genomic organization of single disseminated cancer cells. In some embodiments, the method comprises pre-processing the training dataset. In some embodiments, pre-processing the training dataset comprises transforming the provided data into class-conditional probabilities.

In some embodiments, the genetic information comprises sequence or abundance data from one or more genetic loci in cell-free DNA from the individuals. In some embodiments, the treatment response includes genetic information from the individual generated at a second, later, time point. In some embodiments, the disease state is cancer and the genetic analyzer is a DNA sequencer.

In one aspect, the present disclosure provides a method comprising: using a genetic analyzer to generate genetic information for a subject; receiving into computer memory a test dataset comprising the genetic information; and implementing a computer implemented classification algorithm, wherein the classification algorithm, based on the genetic information, predicts therapeutic response of the subject to a therapeutic intervention.

In some embodiments, the method comprises predicting the development of tumors. In some embodiments, the method comprises predicting the development of distant metastases. In some embodiments, the training dataset further comprises variables selected from the group consisting of: cancer stage, type of surgical procedure, age, tumor grading, depth of tumor infiltration, occurrence of post-operative complications, and the presence of venous invasion. In some embodiments, the genetic information comprises variables defining the genomic organization of cancer cells. In some embodiments, the genetic information comprises variables defining the genomic organization of single disseminated cancer cells. In some embodiments, the method comprises pre-processing the test dataset. In some embodiments, pre-processing the test dataset comprises transforming the provided data into class-conditional probabilities. In some embodiments, 20 variables or fewer are selected. In some embodiments, 10 variables or fewer are selected. In some embodiments, the classification algorithm employs an artificial neural network. In some embodiments, the artificial neural network is trained using a Bayesian framework.

In one aspect, the present disclosure provides a method for analyzing a disease state of a subject, comprising: receiving from a genetic analyzer data about the subject's genetic information at two or more time points; using the information from the two or more time points to produce an adjusted test result in the characterization of the subject's genetic information; identifying from a population subjects with matching genetic information; and recommending a treatment based on prior treatment of subjects with matching genetic information. In some embodiments, the method comprises comparing current sequence reads with prior sequence reads and updating a diagnostic confidence indication accordingly. In some embodiments, the method comprises generating a confidence interval for current sequence reads. In some embodiments, the method comprises comparing the confidence interval with one or more prior confidence intervals and determining a disease progression based on overlapping confidence intervals.

In some embodiments, the method comprises increasing a diagnostic confidence indication in a subsequent or a previous characterization if the information from a first time point corroborates information from the second time point. In some embodiments, characterizing comprises determining a frequency of one of more genetic variants detected among a collection of sequence reads from DNA in a sample from the subject, and producing an adjusted test result comprises comparing frequency of the one or more genetic variants at the two or more time points for the subjects with matching genetic information. In some embodiments, characterizing comprises determining an amount of copy number variation at one or more genetic loci detected from a collection of sequence reads from DNA in a sample from matching subjects, and producing an adjusted test result comprises comparing the amount at the two or more time points. In some embodiments, characterizing comprises making a diagnosis of health or disease.

In some embodiments, the genetic information comprises sequence data from portions of a genome comprising disease-associated or cancer-associated genetic variants. In some embodiments, the method comprises increasing the sensitivity of detecting genetic variants by increasing read depth of polynucleotides in a sample from the subject at two or more time points. In some embodiments, characterizing comprises making a diagnosis of the presence of disease polynucleotides in a sample from the subject, and adjusting comprises adjusting the diagnosis from negative or uncertain to positive when the same genetic variants are detected in the noise range in a plurality of sampling instances or time points. In some embodiments, characterizing comprises making a diagnosis of the presence of disease polynucleotides in a sample from the subject, and adjusting comprises adjusting the diagnosis from negative or uncertain to positive in a characterization from an earlier time point when the same genetic variants are detected in the noise range at the earlier time point and above the noise range at a later time point. In some embodiments, characterizing comprises making a diagnosis of the presence of disease polynucleotides in a sample from the subject, and adjusting comprises adjusting the diagnosis from negative or uncertain to positive in a characterization from an earlier time point when the same genetic variants are detected in the noise range at the earlier time point and above the noise range at a later time point.

In one aspect, the present disclosure provides a method, comprising: a) providing a plurality of nucleic acid samples from a subject, the samples collected at serial time points; b) sequencing polynucleotides from the samples; c) determining a quantitative measure of each of a plurality of somatic mutants among the polynucleotides in each sample; d) graphically representing relative quantities of somatic mutants at each serial time point for those somatic mutations present at a non-zero quantity at least one of the serial time points; and e) correlating mutants from a group of genetically similar subjects and generating treatment recommendations based on prior treatment data for the genetically similar subjects.

In one aspect, the present disclosure provides a method to recommend cancer treatment from data generated by a genetic analyzer, comprising: identifying from a population of cancer persons one or more subjects with matching genetic profiles and retrieving prior treatment data from the matching subjects; and identifying best treatment options based on prior history of the matching subjects; rendering the recommendation on a paper or electronic patient test report. In some embodiments, the method comprises using a combination of a magnitude of detected genomic alterations in a body fluid-based test to infer a disease burden. In some embodiments, the method comprises using allele fractions of detected mutations, allelic imbalances, or gene-specific coverage to infer the disease burden. In some embodiments, an overall stack height is representative of overall disease burden or a disease burden score in the individual. In some embodiments, a distinct color is used to represent each genomic alteration. In some embodiments, only a subset of detected alterations are plotted. In some embodiments, a subset is chosen based on likelihood of being a driver alteration or association with increased or reduced response to treatment. In some embodiments, the method comprises producing a test report for a genomic test. In some embodiments, a non-linear scale is used for representing the heights or widths of each represented genomic alteration. In some embodiments, a plot of previous test points is depicted on the report. In some embodiments, the method comprises estimating a disease progression or remission based on rate of change and/or quantitative precision of each testing result. In some embodiments, the method comprises displaying a therapeutic intervention between intervening testing points.

Other objects of the disclosure may be apparent to one skilled in the art upon reading the following specification and claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1D shows an exemplary process to reduce error rates and bias in DNA sequence readings and generate genetic reports for users based on population test results.

FIGS. 2A-2B show exemplary processes for reporting genetic test results to users and recommending treatments based on population data.

FIGS. 2C-2I show pages from an exemplary genetic test report.

DETAILED DESCRIPTION OF THE INVENTION

Cancer is a particularly heterogeneous disease with respect to both the numerous types of cancer and in how a particular type of cancer manifests in an individual. Because of this, it is difficult to predict the best course of treatment for a given patient. The present disclosure provides systems and methods for improving therapeutic outcomes for cancer patients.

Figure 1A:
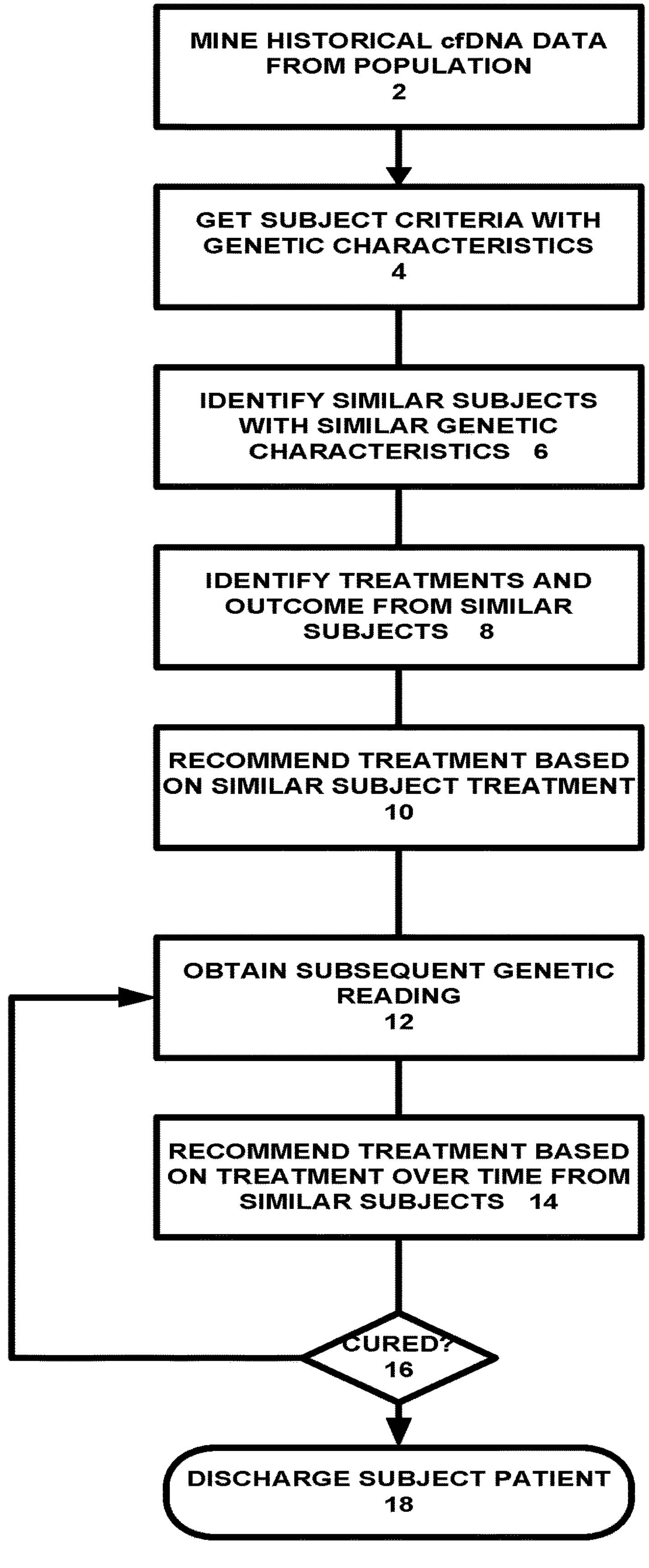
FIG. 1A shows an exemplary population based genetic cancer treatment system.

Referring to FIG. 1A, a population based genetic cancer treatment system is shown. In one embodiment, the system mines historical cell-free DNA (cfDNA) from a population of cancer subjects or patients (2). The mining is done using genetic data captured from patients undergoing treatment or from healthy people. Once the data mining has been done, the system can recommend treatments based on prior successes and by matching the treatment to the subject/patient genetic characteristics. First, the system obtains subject criteria with genetic characteristics (4). Next, the system identifies similar subjects with similar genetic characteristics (6). The system then identifies successful treatments from these similar subjects (8). Based on prior treatments and outcomes for the similar subjects, the system identifies treatments to be recommended for the current subject (10).

Next, the system iteratively monitors the treatment process. This is done through subsequent genetic readings (12). Based on the readings, the system identifies the best matching treatment and recommends the treatment based on the success and the subsequent genetic analysis (14). The system then tracks if the patient has a positive outcome (16). If the patient is not cured, additional treatments are done based on the recommendations by looping back to 12 and otherwise the patient is discharged (18).

Figure 1B:
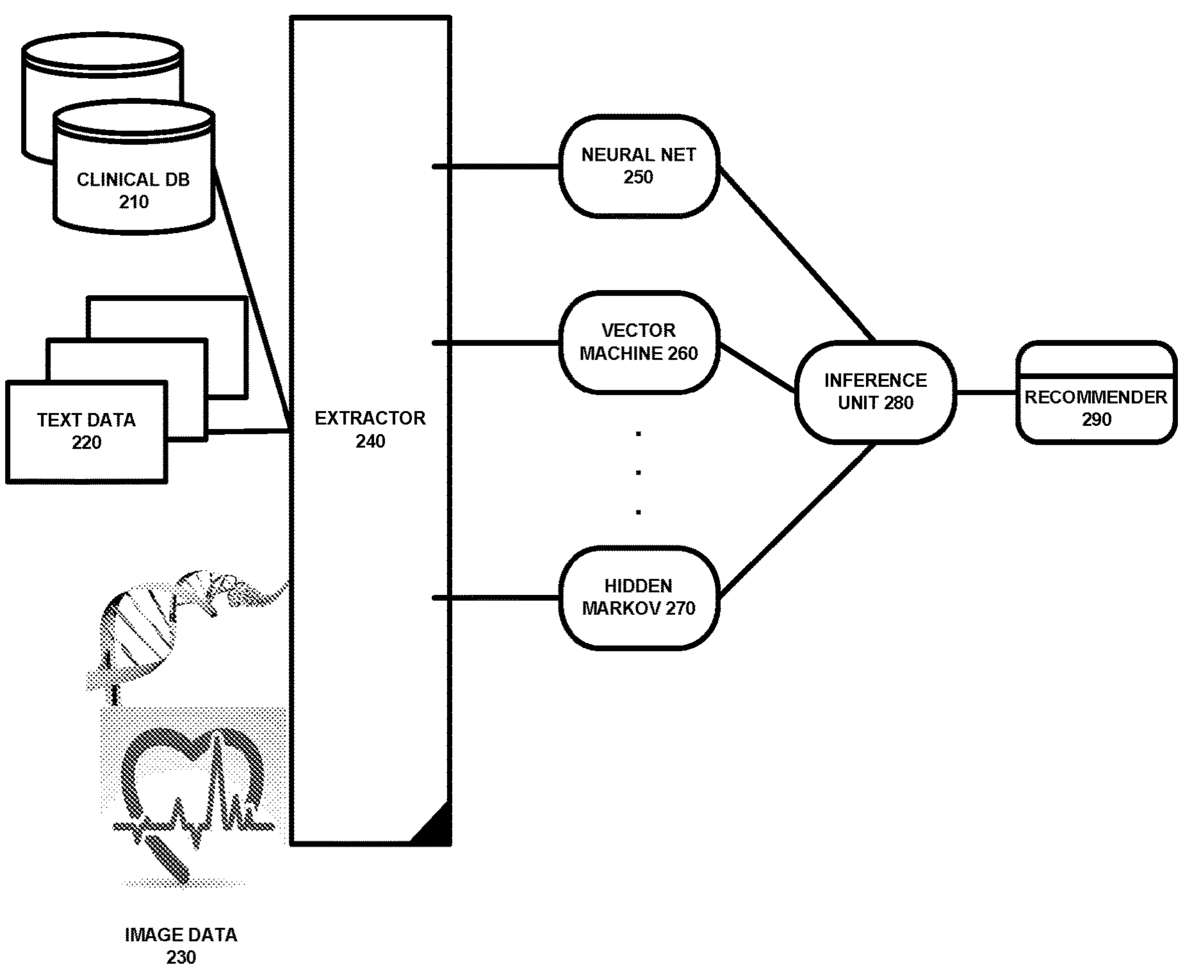
FIG. 1B shows an exemplary recommender population based genetic cancer treatment.

FIG. 1B shows an exemplary recommender 290. In this system, clinical information 210 is stored in a database array. For example, the system can store patient information from physicians and test labs in this database. Text data 220 such as genome sequence is also captured and histology reports for each patients. For example, data can come from cBio Cancer Genomics Portal is an open-access resource for interactive exploration of multidimensional cancer genomics data sets, currently providing access to data from more than 5,000 tumor samples from 20 cancer studies. The cBio Cancer Genomics Portal significantly lowers the barriers between complex genomic data and cancer researchers who want rapid, intuitive, and high-quality access to molecular profiles and clinical attributes from large-scale cancer genomics projects and empowers researchers to translate these rich data sets into biologic insights and clinical applications. Image data 230 such as CT (Computed Tomography) scan can be captured, along with other information such as MRI (Magnetic Resonance Imaging) scan, ultrasound scan, bone scan, PET (Positron Emission Tomography) Scan, bone marrow test, barium X-ray, endoscopy, lymphangiogram, IVU (Intravenous urogram) or IVP (IV pyelogram), lumbar puncture, cystoscopy, immunological tests (anti-malignin antibody screen), and cancer marker tests. Features are then extracted by extractor 240. The features can then be used by one or more classifiers such as neural networks 250, vector machines 260, and Hidden Markov Machines (HMMs) 270. In some embodiments, a neural network is trained using a Bayesian framework. The outputs of the classifiers are then provided to an inference unit or engine 280. The results are provided as the output of a recommender 290, whose result is used in reports by a report generator 21 of FIG. 1C. In some embodiments, data from two or more of the above categories can be utilized to produce a more robust classification than data from a single category.

In some embodiments, the unstructured text is taken from available histology reports. The text is first normalized to reduce basic variations: the formats of acronyms, numbers and dimensions are standardized, relevant abbreviations are expanded, spelling variants are mapped to a common form, and any non-informative character sequences are removed. The set of normalization rules are encoded using regular expressions and implemented using simple search and replace operations.

Some embodiments use a feature-based classifier trained on validated somatic mutation samples while benefiting from other available information such as base quality, mapping quality, strand bias and tail distance. Given paired normal/tumor bam files, the embodiment will output the probability of each candidate site being somatic. Through the systems and methods described herein, the present disclosure provides a way to classify treatment responses to therapeutic interventions, and subsequently determine whether a given individual falls into a particular classification (e.g., responsive to treatment, nonresponsive to treatment, or a particular level of responsiveness such as fully responsive or partially responsive).

In some embodiments, a method is provided for creating a trained classifier, comprising the steps of: (a) providing a plurality of different classes, wherein each class represents a set of subjects with a shared characteristic (e.g. from one or more cohorts); (b) providing a multi-parametric model representative of the cell-free DNA molecules from each of a plurality of samples belonging to each of the classes, thereby providing a training data set; and (c) training a learning algorithm on the training data set to create one or more trained classifiers, wherein each trained classifier classifies a test sample into one or more of the plurality of classes.

As an example, a trained classifier may use a learning algorithm selected from the group consisting of: a random forest, a neural network, a support vector machine, and a linear classifier. Each of the plurality of different classes may be selected from the group consisting of: healthy, breast cancer, colon cancer, lung cancer, pancreatic cancer, prostate cancer, ovarian cancer, melanoma, and liver cancer.

A trained classifier may be applied to a method of classifying a sample from a subject. This method of classifying may comprise: (a) providing a multi-parametric model representative of the cell-free DNA molecules from a test sample from the subject; and (b) classifying the test sample using a trained classifier. After the test sample is classified into one or more classes, a therapeutic intervention on the subject can be performed based on the classification of the sample.

In some embodiments, training sets are provided to a machine learning unit, such as a neural network or a support vector machine. Using the training set, the machine learning unit may generate a model to classify the sample according to a treatment response to one or more therapeutic inventions. This is also referred to as "calling". The model developed may employ information from any part of a test vector.

In some embodiments, DNA from a population of several individuals can be analyzed by a set of multiplexed arrays. The data for each multiplexed array may be self-normalized using the information contained in that specific array. This normalization algorithm may adjust for nominal intensity variations observed in the two color channels, background differences between the channels, and possible crosstalk between the dyes. The behavior of each base position may then be modeled using a clustering algorithm that incorporates several biological heuristics on SNP genotyping. In cases where fewer than three clusters are observed (e.g., due to low minor-allele frequency), locations and shapes of the missing clusters may be estimated using neural networks. Depending on the shapes of the clusters and their relative distance to each other, a statistical score may be devised (a Training score). A score such as GenCall Score is designed to mimic evaluations made by a human expert's visual and cognitive systems. In addition, it has been evolved using the genotyping data from top and bottom strands. This score may be combined with several penalty terms (e.g., low intensity, mismatch between existing and predicted clusters) in order to make up the Training score. The Training score, along with the cluster positions and shapes for each SNP, is saved for use by the calling algorithm.

To call a therapeutic response, a calling algorithm may take the genetic information and treatment responses of a plurality of individuals having a disease or condition. The data may first be normalized (using the same procedure as for the clustering algorithm). The calling operation (classification) may be performed using, for example, a Bayesian model. The score for each call's Call Score can be the product of a Training Score and a data-to-model fit score. After scoring all the treatment responses, the application may compute a composite score.

In some embodiments, a training dataset comprises clinical data selected from the group consisting of cancer stage, type of surgical procedure, age, tumor grading, depth of tumor infiltration, occurrence of post-operative complications, and the presence of venous invasion. In some embodiments, the training dataset is pre-processed, comprising transforming the provided data into class-conditional probabilities.

Another embodiment uses machine learning techniques to train a statistical classifier, specifically a support vector machine, for each cancer stage category based on word occurrences in a corpus of histology reports for each patient. New reports can then be classified according to the most likely stage, facilitating the collection and analysis of population staging data.

Transform data to the format of a support vector machine (SVM) package

Conduct scaling on the data

Consider the RBF kernel

Use cross-validation to find the best parameter C and γ

Use the best parameter C and γ to train the whole training set

Test

Run Live on Patient data

This embodiment uses SVM$^{light}$ which is an open source implementation of Support Vector Machines (SVMs) in C. The main features of the program are the following:

- fast optimization algorithm
- working set selection based on steepest feasible descent
- "shrinking" heuristic
- caching of kernel evaluations
- use of folding in the linear case
- solves classification and regression problems. For multivariate and structured outputs use SVMstruct.
- solves ranking problems (e. g. learning retrieval functions in STRIVER search engine).
- computes XiAlpha-estimates of the error rate, the precision, and the recall
- efficiently computes Leave-One-Out estimates of the error rate, the precision, and the recall
- includes algorithm for approximately training large transductive SVMs (TSVMs) (see also Spectral Graph Transducer)
- can train SVMs with cost models and example dependent costs
- allows restarts from specified vector of dual variables
- handles many thousands of support vectors
- handles several hundred-thousands of training examples
- supports standard kernel functions and lets you define your own
- uses sparse vector representation In some embodiments, a machine learning algorithm is selected from the group consisting of: a supervised or unsupervised learning algorithm selected from support vector machine, random forest, nearest neighbor analysis, linear regression, binary decision tree, discriminant analyses, logistic classifier, and cluster analysis.

Figure 1C:
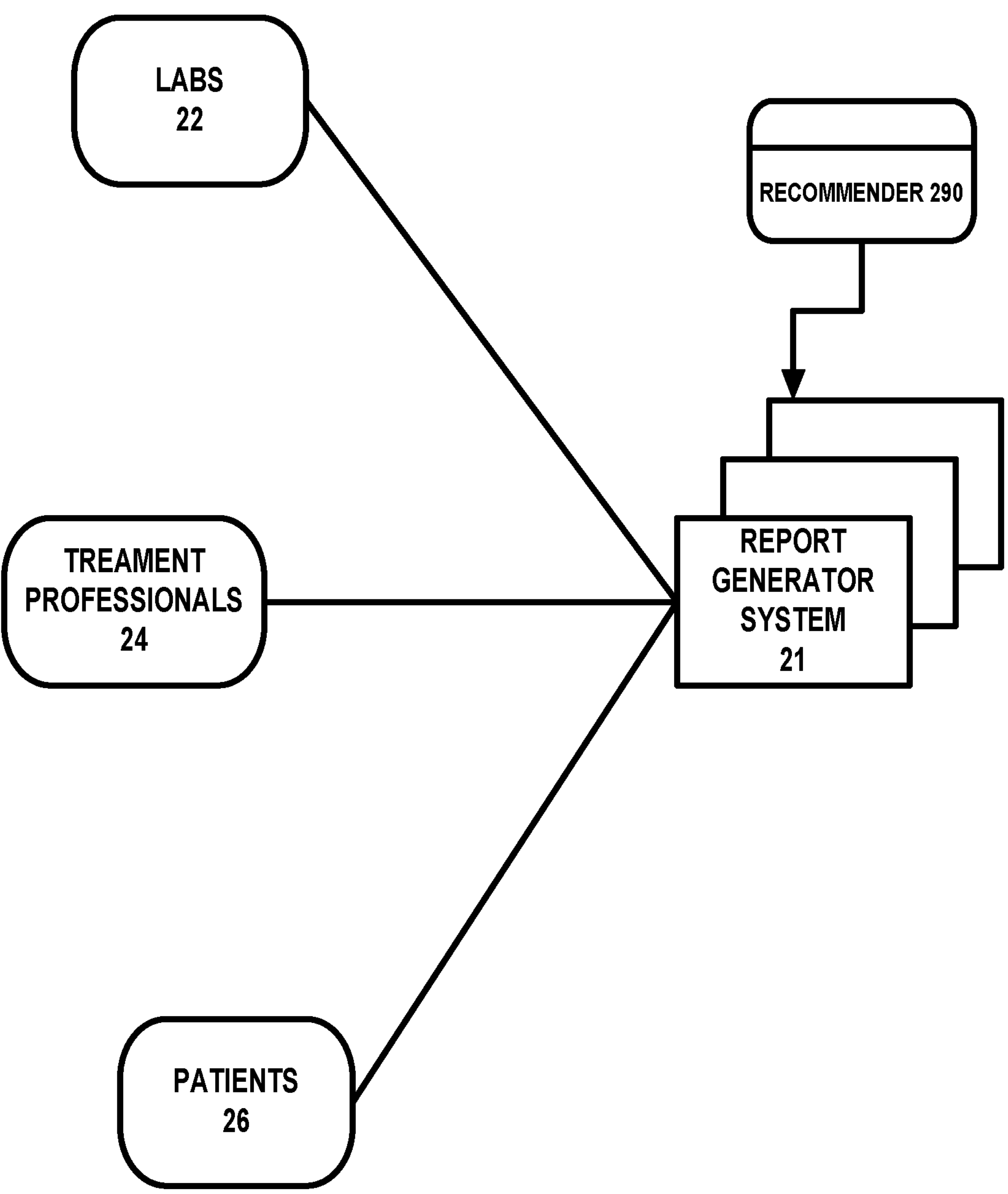
FIG. 1C shows an exemplary system for recommending treatments along with test results.

Referring now to FIG. 1C, a system with a report generator 21 for reporting on cancer test results and treatment options therefrom is schematically illustrated. The report generator system can be a central data processing system configured to establish communications directly with: a remote data site or lab 22, a medical practice/healthcare provider (treating professional) 24 and/or a patient/subject 26 through communication links. The lab 22 can be medical laboratory, diagnostic laboratory, medical facility, medical practice, point-of-care testing device, or any other remote data site capable of generating subject clinical information. Subject clinical information includes but it is not limited to laboratory test data, X-ray data, examination and diagnosis. The healthcare provider or practice 26 includes medical services providers, such as doctors, nurses, home health aides, technicians and physician's assistants, and the practice is any medical care facility staffed with healthcare providers. In certain instances the healthcare provider/practice is also a remote data site. In a cancer treatment embodiment, the subject may be afflicted with cancer, among others.

Other clinical information for a cancer subject 26 includes the results of laboratory tests, imaging or medical procedure directed towards the specific cancer that one of ordinary skill in the art can readily identify. The list of appropriate sources of clinical information for cancer includes but it is not limited to: CT (Computed Tomography) scan, MRI (Magnetic Resonance Imaging) scan, ultrasound scan, bone scan, PET (Positron Emission Tomography) Scan, bone marrow test, barium X-ray, endoscopy, lymphangiogram, IVU (Intravenous urogram) or IVP (IV pyelogram), lumbar puncture, cystoscopy, immunological tests (anti-malignin antibody screen), and cancer marker tests.

The subject 26's clinical information may be obtained from the lab 22 manually or automatically. For simplicity of the system the information is obtained automatically at predetermined or regular time intervals. A regular time interval refers to a time interval at which the collection of the laboratory data is carried out automatically by the methods and systems described herein based on a measurement of time such as hours, days, weeks, months, years etc. In one embodiment of the invention, the collection of data and processing is carried out at least once a day. In one embodiment, the transfer and collection of data is carried out once every month, biweekly, or once a week, or once every couple of days. Alternatively the retrieval of information may be carried out at predetermined but not regular time intervals. For instance, a first retrieval step may occur after one week and a second retrieval step may occur after one month. The transfer and collection of data can be customized according to the nature of the disorder that is being managed and the frequency of required testing and medical examinations of the subjects.

FIG. 1D shows an exemplary process to generate genetic reports, including a tumor response map and associated summary of alterations. This process reduces error rates and bias that can be orders of magnitude higher than what is required to reliably detect de novo genomic alterations associated with cancer. The process first captures genetic information by collecting body fluid samples as sources of genetic material (e.g., blood, serum, plasma, urine, cerebrospinal fluid, saliva, stool, lymph fluid, synovial fluid, cystic fluid, ascites, pleural effusion, amniotic fluid, chorionic villus sample, fluid from a preimplantation embryo, a placental sample, lavage and cervical vaginal fluid, interstitial fluid, a buccal swab sample, sputum, bronchial lavage, a Pap smear sample, or ocular fluid) and then the process sequences the materials (71). For example, polynucleotides in a sample can be sequenced, producing a plurality of sequence reads. The tumor burden in a sample that comprises polynucleotides can be estimated as the relative number of sequence reads bearing a variant, to the total number of sequence reads generated from the sample. Also, in the case of copy number variants, the tumor burden can be estimated as the relative excess (in the case of gene duplication) or relative deficit (in the case of gene elimination) of total number of sequence reads at test and control loci. So, for example, a run may produce 1000 reads mapping to an oncogene locus, of which 900 correspond to wild type and 100 correspond to a cancer mutant, indicating a copy number variant at this gene. In some embodiments, genetic information comprises variables defining the genomic organization of cancer cells or the genomic organization of single disseminated cancer cells. In some embodiments, the genetic information comprises sequence or abundance data from one or more genetic loci in cell-free DNA from the individuals. More details on exemplary specimen collection and sequencing of the genetic materials are discussed below in FIGS. 3A-3B.

Next, genetic information is processed (72). Genetic variants are then identified. Genetic variants include sequence variants, copy number variants and nucleotide modification variants. A sequence variant is a variation in a genetic nucleotide sequence. A copy number variant is a deviation from wild type in the number of copies of a portion of a genome. Genetic variants include, for example, single nucleotide variations (SNPs), insertions, deletions, inversions, transversions, translocations, gene fusions, chromosome fusions, gene truncations, copy number variations (e.g., aneuploidy, partial aneuploidy, polyploidy, gene amplification), abnormal changes in nucleic acid chemical modifications, abnormal changes in epigenetic patterns and abnormal changes in nucleic acid methylation. The process then determines the frequency of genetic variants in the sample containing the genetic material. Since this process is noisy, the process separates information from noise (73). The sensitivity of detecting genetic variants can be increased by increasing read depth of polynucleotides (e.g., by sequencing to a greater read depth at in a sample from a subject at two or more time points).

Sequencing methods have error rates. For example, the mySeq system of Illumina can produce percent error rates in the low single digits. Thus, for 1000 sequence reads mapping to a locus, one might expect about 50 reads (about 5%) to include errors. Certain methodologies, such as those described in WO 2014/149134 (Talasaz and Eltoukhy) can significantly reduce the error rate. Errors create noise that can obscure signals from cancer present at low levels in a sample. Thus, if a sample has a tumor burden at a level around the sequencing system error rate, e.g., around 0.1%-5%, it may be difficult to distinguish a signal corresponding to a genetic variant due to cancer from one due to noise.

Diagnosis of cancer can be done by analyzing the genetic variants, even in the presence of noise. The analysis can be based on the frequency of Sequence Variants or Level of CNV (74) and a diagnosis confidence indication or level for detecting genetic variants in the noise range can be established (75).

Next, the process increases the diagnosis confidence. This can be done using a plurality of measurements to increase confidence of diagnosis (6), or alternatively using measurements at a plurality of time points (e.g., 2, 3, 4, 5, 6, 7, 8, 9, 10, or more time points) to determine whether cancer is advancing, in remission or stabilized (77). The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden."

Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

Next, the process generates genetic Report/Diagnosis. First, the process retrieves Prior Treatment from the Population with Similar Genetic Profile (78). The process includes generating genetic graph for a plurality of measurements showing mutation trend (79) and generating report showing treatment results and options (80).

One application is the detection of cancer. Numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as mutations. This phenomenon may be used to detect the presence or absence of cancers individuals using the methods and systems described herein For example, blood from subjects at risk for cancer may be drawn and prepared as described herein to generate a population of cell free polynucleotides. In one example, this might be cell free DNA. The systems and methods of the disclosure may be employed to detect mutations or copy number variations that may exist in certain cancers present. The method may help detect the presence of cancerous cells in the body, despite the absence of symptoms or other hallmarks of disease.

As used herein, the term "cancer" includes, but is not limited to, various types of malignant neoplasms, most of which can invade surrounding tissues, and may metastasize to different sites (see, for example, PDR Medical Dictionary, 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Such abnormal tissue shows partial or complete lack of structural organization and functional coordination with the normal tissue which may be either benign (such as a benign tumor) or malignant (such as a malignant tumor). Examples of general categories of cancer include, but are not limited to, carcinomas (malignant tumors derived from epithelial cells such as, for example, common forms of breast, prostate, lung and colon cancer), sarcomas (malignant tumors derived from connective tissue or mesenchymal cells), lymphomas (malignancies derived from hematopoietic cells), leukemias (malignancies derived from hematopoietic cells), and germ cell tumors (tumors derived from totipotent cells, in adults most often found in the testicle or ovary; in fetuses, babies and young children, most often found on the body midline, particularly at the tip of the tailbone), blastic tumors (a typically malignant tumor which resembles an immature or embryonic tissue) and the like. Examples of the types of neoplasms intended to be encompassed by the present invention include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys. In particular embodiments, types and number of cancers that may be detected include, but are not limited to, blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

In the early detection of cancers, any of the systems or methods herein described, including mutation detection or copy number variation detection may be utilized to detect cancers. These system and methods may be used to detect any number of genetic aberrations that may cause or result from cancers. These may include but are not limited to mutations, mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

The systems and methods provided herein may be used to monitor already known cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In one example, successful treatment options may actually increase the amount of copy number variation or mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein may not be limited to detection of mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and mutations that could be observed. In another example, the system and methods of the disclosure may also be used to monitor the genomes of immune cells within the body. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the systems and methods of this disclosure may also be used to monitor systemic infections themselves, as may be caused by a pathogen such as a bacteria or virus. Copy number variation or even mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection.

Yet another example that the system and methods of this disclosure may be used for is the monitoring of transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site (also known as distant metastases).

The methods of this disclosure may be used to generate a profile, fingerprint, or set of data that is a summation of genetic information derived from different cells in a heterogeneous disease. This set of data may comprise copy number variation and mutation analyses alone or in combination.

Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer (formerly the European Journal of Cancer and Clinical Oncology), Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, and Radiation Oncology.

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The report and the annotated information can be provided on a printed form, and the annotations can be, for example, a footnote to a reference.

The information for annotating one or more drug treatment options in a report can be provided by a commercial entity that stores scientific information, for example. A health care provider can treat a subject, such as a cancer subject, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company. The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc. The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The provided methods can also include means for investigating the effects of drugs on sample (e.g. tumor cells) isolated from a subject (e.g. cancer subject). An in vitro culture using a tumor from a cancer subject can be established using techniques known to those skilled in the art. The provided method can also include high-throughput screening of FDA approved off-label drugs or experimental drugs using said in vitro culture and/or xenograft model. The provided method can also include monitoring tumor antigen for recurrence detection.

Reports are generated, mapping genome positions and copy number variation for the subject with cancer. These reports, in comparison to other profiles of subjects with known outcomes, can indicate that a particular cancer is aggressive and resistant to treatment. The subject is monitored for a period and retested. If at the end of the period, the copy number variation profile begins to increase dramatically, this may indicate that the current treatment is not working. A comparison is done with genetic profiles of other prostate subjects. For example, if it is determined that this increase in copy number variation indicates that the cancer is advancing, then the original treatment regimen as prescribed is no longer treating the cancer and a new treatment is prescribed.

Figure 2A:
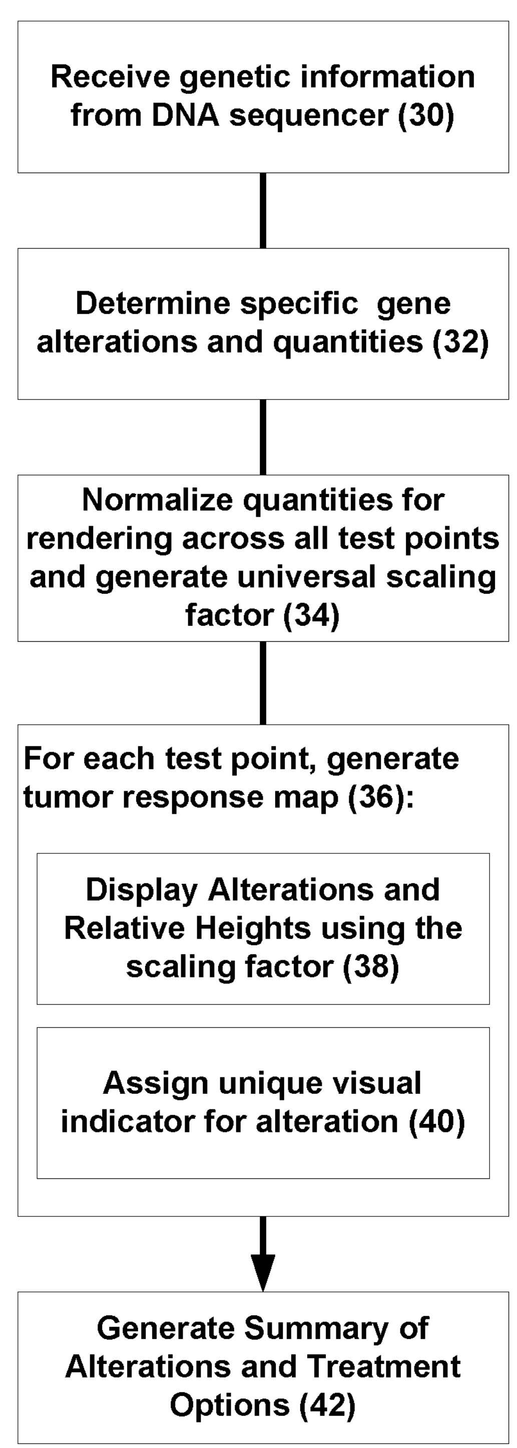
Figure 2I:
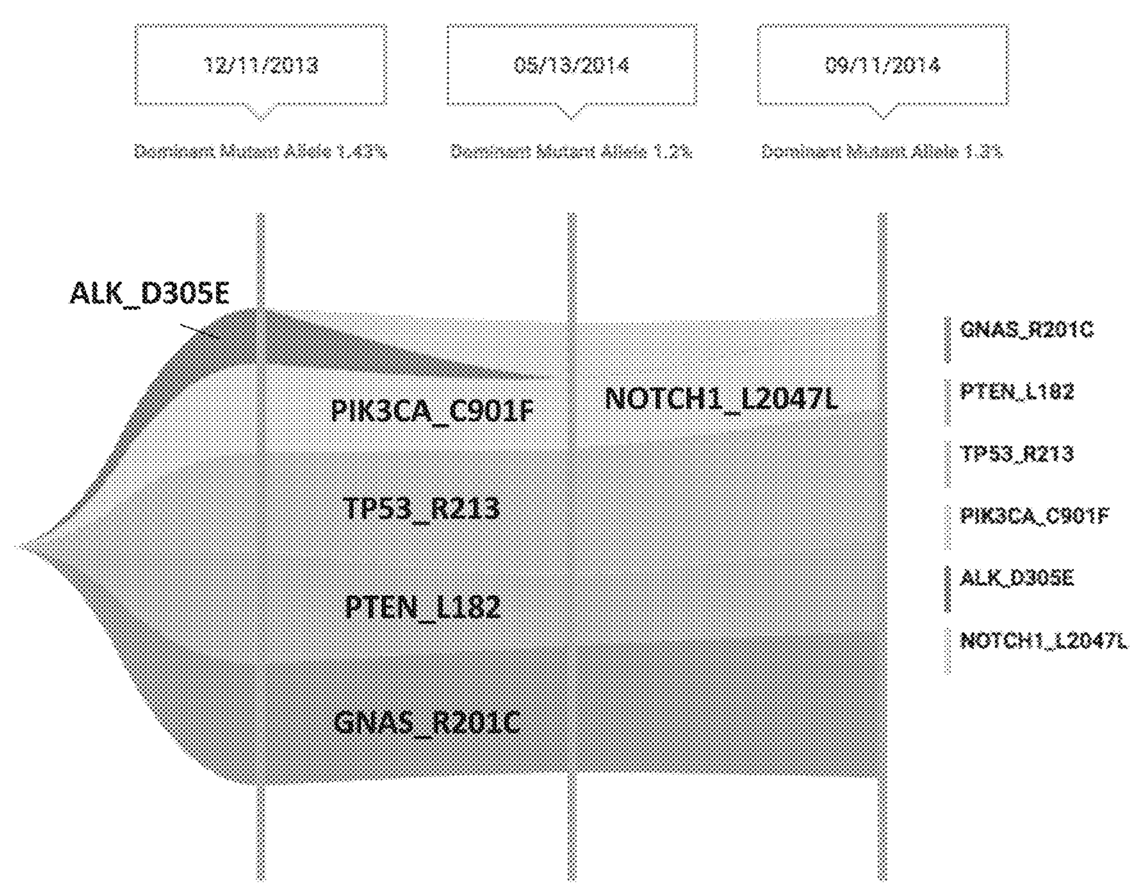

FIGS. 2A-2B show in more details one embodiment for generating genetic reports and diagnosis. In one implementation, FIG. 2B shows an exemplary pseudo-code executed by the system of FIG. 1A to process non-CNV reported mutant allele frequencies. However, the system can process CNV reported mutant allele frequencies as well.

Turning now to FIG. 2A, the process receives genetic information from a DNA sequencer (30). The process then determines specific gene alterations and quantities thereof (32). Next, a tumor response map is generated. To generate the map, the process normalizes the quantities for each gene alteration for rendering across all test points and then generates a scaling factor (34). As used herein, the term "normalize" generally refers to means adjusting values measured on different scales to a notionally common scale. For example, data measured at different points are converted/adjusted so that all values can be resized to a common scale. As used herein, the term "scaling factor" generally refers to a number which scales, or multiplies, some quantity. For example, in the equation y=Cx, C is the scale factor for x. C is also the coefficient of x, and may be called the constant of proportionality of y to x. The values are normalized to allow plotting on a common scale that is visually-friendly. And the scaling factor is used to know the exact heights that correspond to the values to be plotted (e.g. 10% mutant allele frequency means say 1 cm on the report). The scaling factor is applied to all test points and thus is considered to be a universal scaling factor. For each test point, the process renders information on a tumor response map (36). In operation 36, the process renders alterations and relative heights using the determined scaling factor (42) and assigns a unique visual indicator for each alteration. In addition to the response map, the process generates a summary of alterations and treatment options. Also, information from clinical trials that may help the particular genetic alterations and other helpful treatment suggestions is presented, along with explanations of terminology, test methodology, and other information is added to the report and rendered for the user.

In one implementation, the copy number variation may be reported as graph, indicating various positions in the genome and a corresponding increase or decrease or maintenance of copy number variation at each respective position. Additionally, copy number variation may be used to report a percentage score indicating how much disease material (or nucleic acids having a copy number variation) exists in the cell free polynucleotide sample.

These reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

Figure 3A:
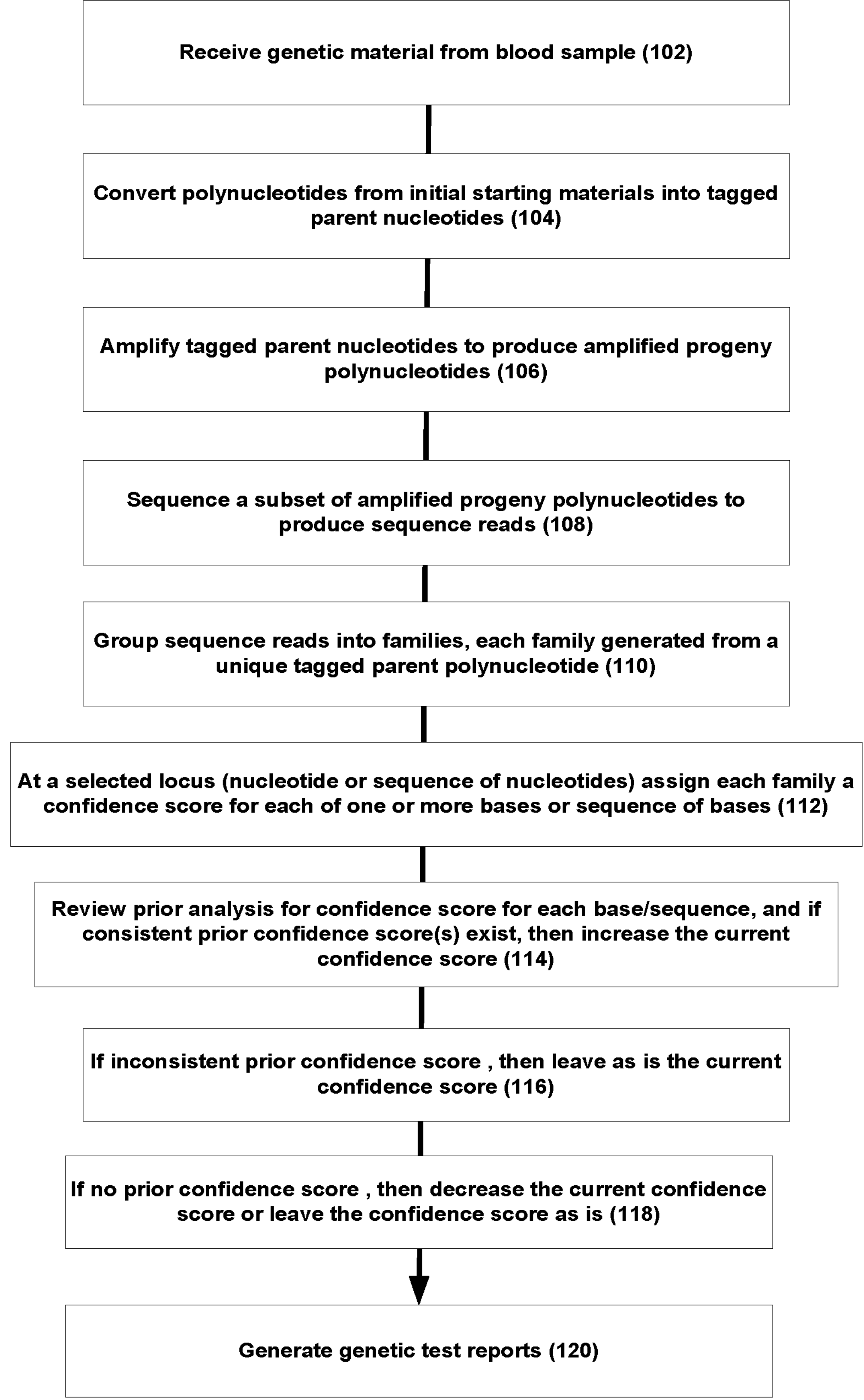
FIGS. 3A-3B shows exemplary processes for detecting mutation and reporting test results to users.

Next, details of exemplary gene testing processes are disclosed. Turning now to FIG. 3A, an exemplary process receives genetic materials from blood sample or other body samples (102). The process converts the polynucleotides from the genetic materials into tagged parent nucleotides (104). The tagged parent nucleotides are amplified to produce amplified progeny polynucleotides (106). A subset of the amplified polynucleotides is sequenced to produce sequence reads (108, which are grouped into families, each generated from a unique tagged parent nucleotide (110). At a selected locus, the process assigns each family a confidence score for each family (112). Next, a consensus is determined using prior readings. This is done by reviewing prior confidence score for each family, and if consistent prior confidence scores exists, then the current confidence score is increased (114). If there are prior confidence scores, but they are inconsistent, the current confidence score is not modified in one embodiment (116). In other embodiments, the confidence score is adjusted in a predetermined manner for inconsistent prior confidence scores. If this is a first time the family is detected, the current confidence score can be reduced as it may be a false reading (118). The process can infer the frequency of the family at the locus in the set of tagged parent polynucleotides based on the confidence score. Then genetic test reports are generated as discussed above (120).

In some embodiments, only a subset of detected alterations are plotted. In some embodiments, a subset is chosen based on likelihood of being a driver alteration or association with increased or reduced response to treatment. In some embodiment, a combination of a magnitude of detected genomic alterations in a body fluid-based test is used to infer a disease burden. In some embodiments, allele fractions of detected mutations, allelic imbalances, or gene-specific coverage is used to infer the disease burden. In some embodiments, an overall stack height is representative of overall disease burden or a disease burden score in the subject. In some embodiments, a distinct color is used to represent each genetic variant. In some embodiments, only a subset of detected genetic variants is plotted. In some embodiments, the subset is chosen based on likelihood of being a driver alteration or association with increased or reduced response to treatment.

Figure 3B:
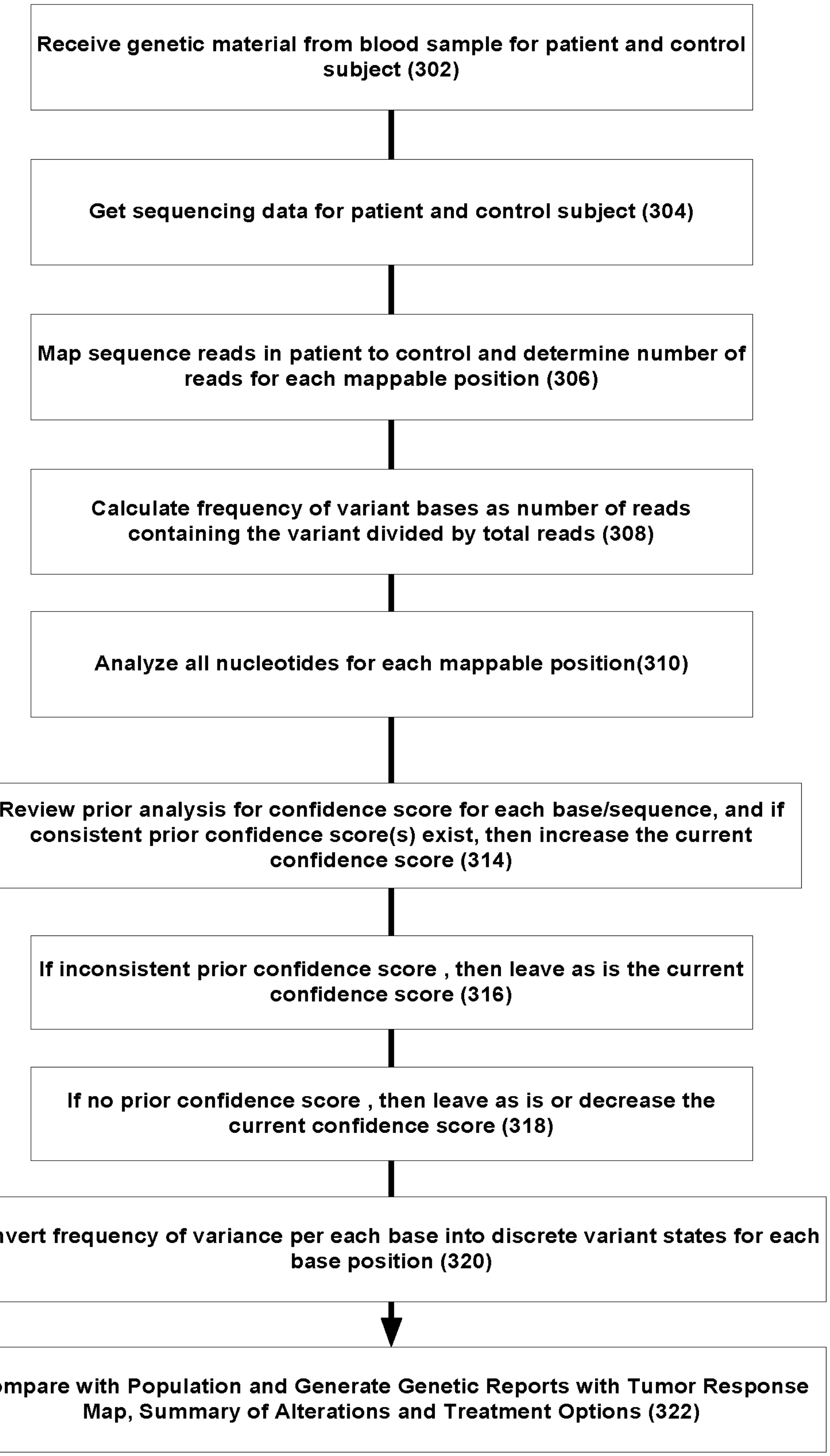

While temporal information has been used in FIGS. 3A-3B to enhance the information for mutation or copy number variation detection, other consensus methods can be applied. In other embodiments, the historical comparison can be used in conjunction with other consensus sequences mapping to a particular reference sequence to detect instances of genetic variation. Consensus sequences mapping to particular reference sequences can be measured and normalized against control samples. Measures of molecules mapping to reference sequences can be compared across a genome to identify areas in the genome in which copy number varies, or heterozygosity is lost. Consensus methods include, for example, linear or non-linear methods of building consensus sequences (such as voting, averaging, statistical, maximum a posteriori or maximum likelihood detection, dynamic programming, Bayesian, hidden Markov or support vector machine methods, etc.) derived from digital communication theory, information theory, or bioinformatics. After the sequence read coverage has been determined, a stochastic modeling algorithm is applied to convert the normalized nucleic acid sequence read coverage for each window region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies and neural networks.

Artificial neural networks (NNets) mimic networks of "neurons" based on the neural structure of the brain. They process records one at a time, or in a batch mode, and "learn" by comparing their classification of the record (which, at the outset, is largely arbitrary) with the known actual classification of the record. In MLP-NNets, the errors from the initial classification of the first record is fed back into the network, and are used to modify the network's algorithm the second time around, and so on for many iterations.

The neural networks uses an iterative learning process in which data cases (rows) are presented to the network one at a time, and the weights associated with the input values are adjusted each time.

After all cases are presented, the process often starts over again. During this learning phase, the network learns by adjusting the weights so as to be able to predict the correct class label of input samples. Neural network learning is also referred to as "connectionist learning," due to connections between the units. Advantages of neural networks include their high tolerance to noisy data, as well as their ability to classify patterns on which they have not been trained. One neural network algorithm is back-propagation algorithm, such as Levenberg-Marquadt. Once a network has been structured for a particular application, that network is ready to be trained. To start this process, the initial weights are chosen randomly. Then the training, or learning, begins.

The network processes the records in the training data one at a time, using the weights and functions in the hidden layers, then compares the resulting outputs against the desired outputs. Errors are then propagated back through the system, causing the system to adjust the weights for application to the next record to be processed. This process occurs over and over as the weights are continually tweaked. During the training of a network the same set of data is processed many times as the connection weights are continually refined.

In an embodiment, the training step of the machine learning unit on the training data set may generate one or more classification models for applying to a test sample. These classification models may be applied to a test sample to predict the response of a subject to a therapeutic intervention.

As depicted in FIG. 3B, a comparison of sequence coverage to a control sample or reference sequence may aid in normalization across windows. In this embodiment, cell free DNAs are extracted and isolated from a readily accessible bodily fluid such as blood. For example, cell free DNAs can be extracted using a variety of methods known in the art, including but not limited to isopropanol precipitation and/or silica based purification. Cell free DNAs may be extracted from any number of subjects, such as subjects without cancer, subjects at risk for cancer, or subjects known to have cancer (e.g. through other means).

Following the isolation/extraction step, any of a number of different sequencing operations may be performed on the cell free polynucleotide sample. Samples may be processed before sequencing with one or more reagents (e.g., enzymes, unique identifiers (e.g., barcodes), probes, etc.). In some cases if the sample is processed with a unique identifier such as a barcode, the samples or fragments of samples may be tagged individually or in subgroups with the unique identifier. The tagged sample may then be used in a downstream application such as a sequencing reaction by which individual molecules may be tracked to parent molecules.

The cell free polynucleotides can be tagged or tracked in order to permit subsequent identification and origin of the particular polynucleotide. The assignment of an identifier (e.g., a barcode) to individual or subgroups of polynucleotides may allow for a unique identity to be assigned to individual sequences or fragments of sequences. This may allow acquisition of data from individual samples and is not limited to averages of samples. In some examples, nucleic acids or other molecules derived from a single strand may share a common tag or identifier and therefore may be later identified as being derived from that strand. Similarly, all of the fragments from a single strand of nucleic acid may be tagged with the same identifier or tag, thereby permitting subsequent identification of fragments from the parent strand. In other cases, gene expression products (e.g., mRNA) may be tagged in order to quantify expression, by which the barcode, or the barcode in combination with sequence to which it is attached can be counted. In still other cases, the systems and methods can be used as a PCR amplification control. In such cases, multiple amplification products from a PCR reaction can be tagged with the same tag or identifier. If the products are later sequenced and demonstrate sequence differences, differences among products with the same identifier can then be attributed to PCR error. Additionally, individual sequences may be identified based upon characteristics of sequence data for the read themselves. For example, the detection of unique sequence data at the beginning (start) and end (stop) portions of individual sequencing reads may be used, alone or in combination, with the length, or number of base pairs of each sequence read unique sequence to assign unique identities to individual molecules. Fragments from a single strand of nucleic acid, having been assigned a unique identity, may thereby permit subsequent identification of fragments from the parent strand. This can be used in conjunction with bottlenecking the initial starting genetic material to limit diversity.

Further, using unique sequence data at the beginning (start) and end (stop) portions of individual sequencing reads and sequencing read length may be used, alone or combination, with the use of barcodes. In some cases, the barcodes may be unique as described herein. In other cases, the barcodes themselves may not be unique. In this case, the use of non-unique barcodes, in combination with sequence data at the beginning (start) and end (stop) portions of individual sequencing reads and sequencing read length may allow for the assignment of a unique identity to individual sequences. Similarly, fragments from a single strand of nucleic acid having been assigned a unique identity, may thereby permit subsequent identification of fragments from the parent strand.

Generally, the methods and systems provided herein are useful for preparation of cell free polynucleotide sequences to a down-stream application sequencing reaction. Often, a sequencing method is classic Sanger sequencing.

As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET (Positron Emission Tomography) sequencing, and a combination thereof. In some embodiments, sequencing can be performer by a gene analyzer such as, for example, gene analyzers commercially available from Illumina or Applied Biosystems. In some embodiments, the sequencing method can be massively parallel sequencing, that is, simultaneously (or in rapid succession) sequencing any of at least 100, 1000, 10,000, 100,000, 1 million, 10 million, 100 million, or 1 billion polynucleotide molecules.

Sequencing methods typically involve sample preparation, sequencing of polynucleotides in the prepared sample to produce sequence reads and bioinformatic manipulation of the sequence reads to produce quantitative and/or qualitative genetic information about the sample. Sample preparation typically involves converting polynucleotides in a sample into a form compatible with the sequencing platform used. This conversion can involve tagging polynucleotides. In certain embodiments of this invention the tags comprise polynucleotide sequence tags. Conversion methodologies used in sequencing may not be 100% efficient. For example, it is not uncommon to convert polynucleotides in a sample with a conversion efficiency of about 1-5%, that is, about 1-5% of the polynucleotides in a sample are converted into tagged polynucleotides. Polynucleotides that are not converted into tagged molecules are not represented in a tagged library for sequencing. Accordingly, polynucleotides having genetic variants represented at low frequency in the initial genetic material may not be represented in the tagged library and, therefore may not be sequenced or detected. By increasing conversion efficiency, the probability that a polynucleotide in the initial genetic material will be represented in the tagged library and, consequently, detected by sequencing is increased. Furthermore, rather than directly address the low conversion efficiency issue of library preparation, most protocols to date call for greater than 1 microgram of DNA as input material. However, when input sample material is limited or detection of polynucleotides with low representation is desired, high conversion efficiency can efficiently sequence the sample and/or to adequately detect such polynucleotides.

Generally, mutation detection may be performed on selectively enriched regions of the genome or transcriptome purified and isolated (302). As described herein, specific regions, which may include but are not limited to genes, oncogenes, tumor suppressor genes, promoters, regulatory sequence elements, non-coding regions, miRNAs, snRNAs and the like may be selectively amplified from a total population of cell free polynucleotides. This may be performed as herein described. In one example, multiplex sequencing may be used, with or without barcode labels for individual polynucleotide sequences. In other examples, sequencing may be performed using any nucleic acid sequencing platforms known in the art. This step generates a plurality of genomic fragment sequence reads (304). Additionally, a reference sequence is obtained from a control sample, taken from another subject. In some cases, the control subject may be a subject known to not have known genetic aberrations or disease. In some cases, these sequence reads may contain barcode information. In other examples, barcodes are not utilized.

After sequencing, reads are assigned a quality score. A quality score may be a representation of reads that indicates whether those reads may be useful in subsequent analysis based on a threshold. In some cases, some reads are not of sufficient quality or length to perform the subsequent mapping step. Sequencing reads with a quality score at least 90%, 95%, 99%, 99.9%, 99.99% or 99.999% may be filtered out of the data set. In other cases, sequencing reads assigned a quality scored at least 90%, 95%, 99%, 99.9%, 99.99% or 99.999% may be filtered out of the data set. In step 306, the genomic fragment reads that meet a specified quality score threshold are mapped to a reference genome, or a reference sequence that is known not to contain mutations. After mapping alignment, sequence reads are assigned a mapping score. A mapping score may be a representation or reads mapped back to the reference sequence indicating whether each position is or is not uniquely mappable. In instances, reads may be sequences unrelated to mutation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

For each mappable base, bases that do not meet the minimum threshold for mappability, or low quality bases, may be replaced by the corresponding bases as found in the reference sequence.

Once read coverage may be ascertained and variant bases relative to the control sequence in each read are identified, the frequency of variant bases may be calculated as the number of reads containing the variant divided by the total number of reads. This may be expressed as a ratio for each mappable position in the genome.

For each base position, the frequencies of all four nucleotides, cytosine, guanine, thymine, adenine are analyzed in comparison to the reference sequence. A stochastic or statistical modeling algorithm is applied to convert the normalized ratios for each mappable position to reflect frequency states for each base variant. In some cases, this algorithm may comprise one or more of the following: Hidden Markov Model, dynamic programming, support vector machine, Bayesian or probabilistic modeling, trellis decoding, Viterbi decoding, expectation maximization, Kalman filtering methodologies, and neural networks.

In step 312, the discrete mutation states of each base position can be utilized to identify a base variant with high frequency of variance as compared to the baseline of the reference sequence. In some cases, the baseline might represent a frequency of at least 0.0001%, 0.001%, 0.01%, 0.1%, 1.0%, 2.0%, 3.0%, 4.0% 5.0%, 10%, or 25%. In other cases the baseline might represent a frequency of at least 0.0001%, 0.001%, 0.01%, 0.1%, 1.0%, 2.0%, 3.0%, 4.0% 5.0%. 10%, or 25%. In some cases, all adjacent base positions with the base variant or mutation can be merged into a segment to report the presence or absence of a mutation. In some cases, various positions can be filtered before they are merged with other segments.

After calculation of frequencies of variance for each base position, the variant with largest deviation for a specific position in the sequence derived from the subject as compared to the reference sequence is identified as a mutation. In some cases, a mutation may be a cancer mutation. In other cases, a mutation might be correlated with a disease state.

A mutation or variant may comprise a genetic aberration that includes, but is not limited to a single base substitution, or small indels, transversions, translocations, inversion, deletions, truncations or gene truncations. In some cases, a mutation may be at most 1, 2, 3, 4, 5, 6, 7, 8, 9, 10, 15 or 20 nucleotides in length. On other cases a mutation may be at least 1, 2, 3, 4, 5, 6, 7, 8, 9, 10, 15 or 20 nucleotides in length.

Next, a consensus is determined using prior readings. This is done by reviewing prior confidence score for the corresponding bases, and if consistent prior confidence scores exists, then the current confidence score is increased (314). If there are prior confidence scores, but they are inconsistent, the current confidence score is not modified in one embodiment (316). In other embodiments, the confidence score is adjusted in a predetermined manner for inconsistent prior confidence scores. If this is a first time the family is detected, the current confidence score can be reduced as it may be a false reading (318). The process then converts the frequency of variance per each base into discrete variant states for each base position (320).

Numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as mutations. This phenomenon may be used to detect the presence or absence of cancers individuals using the methods and systems described herein.

For example, blood from subjects at risk for cancer may be drawn and prepared as described herein to generate a population of cell free polynucleotides. In one example, this might be cell free DNA. The systems and methods of the disclosure may be employed to detect mutations or copy number variations that may exist in certain cancers present. The method may help detect the presence of cancerous cells in the body, despite the absence of symptoms or other hallmarks of disease.

The types and number of cancers that may be detected may include but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

The system and methods may be used to detect any number of genetic aberrations that may cause or result from cancers. These may include but are not limited to mutations, mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

The systems and methods provided herein may be used to monitor already known cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In one example, successful treatment options may actually increase the amount of copy number variation or mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein may not be limited to detection of mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and mutations that could be observed. In another example, the system and methods of the disclosure may also be used to monitor the genomes of immune cells within the body. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the systems and methods of this disclosure may also be used to monitor systemic infections themselves, as may be caused by a pathogen such as a bacteria or virus. Copy number variation or even mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection.

Yet another example that the system and methods of this disclosure may be used for is the monitoring of transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The methods of this disclosure may be used to generate or profile, fingerprint or set of data that is a summation of genetic information derived from different cells in a heterogeneous disease. This set of data may comprise copy number variation and mutation analyses alone or in combination.

Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer (formerly the European Journal of Cancer and Clinical Oncology), Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, and Radiation Oncology.

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The report and the annotated information can be provided on a printed form, and the annotations can be, for example, a footnote to a reference.

The information for annotating one or more drug treatment options in a report can be provided by a commercial entity that stores scientific information. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc.

The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The system can also include reports on the effects of drugs on sample (e.g. tumor cells) isolated from a subject (e.g. cancer patient). An in vitro culture using a tumor from a cancer patient can be established using techniques known to those skilled in the art. The system can also include high-throughput screening of FDA approved off-label drugs or experimental drugs using said in vitro culture and/or xenograft model. The system can also include monitoring tumor antigen for recurrence detection.

The system can provide internet enabled access of reports of a subject with cancer. The system can use a handheld DNA sequencer or a desktop DNA sequencer. The DNA sequencer is a scientific instrument used to automate the DNA sequencing process. Given a sample of DNA, a DNA sequencer is used to determine the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides.

The DNA sequencer can apply Gilbert's sequencing method based on chemical modification of DNA followed by cleavage at specific bases, or it can apply Sanger's technique which is based on dideoxynucleotide chain termination. The Sanger method became popular due to its increased efficiency and low radioactivity. The DNA sequencer can use techniques that do not require DNA amplification (polymerase chain reaction—PCR), which speeds up the sample preparation before sequencing and reduces errors. In addition, sequencing data is collected from the reactions caused by the addition of nucleotides in the complementary strand in real time. For example, the DNA sequencers can utilize a method called Single-molecule real-time (SMRT), where sequencing data is produced by light (captured by a camera) emitted when a nucleotide is added to the complementary strand by enzymes containing fluorescent dyes. Alternatively, the DNA sequencers can use electronic systems based on nanopore sensing technologies.

The data is sent by the DNA sequencers over a direct connection or over the internet to a computer for processing. The data processing aspects of the system can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object-oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:

obtaining or having obtained a cell-free biological sample comprising cell-free DNA (cfDNA) molecules from a subject from at least two different time points;

generating a plurality of sequencing reads from the cfDNA molecules;

identifying, in the plurality of sequencing reads, genetic variants comprising sequence variants and copy number variants;

quantifying the frequency of genetic variants;

generating an initial diagnostic confidence indication based on the genetic variants and frequencies of the genetic variants from the first of the at least two different time points;

generating an adjusted diagnostic confidence indication based on conflict or corroboration of the genetic variants and frequencies of the genetic variants from the second of the at least two different time points;

storing genetic information comprising the genetic variants and frequencies of the genetic variants and clinical information comprising initial and adjusted diagnostic confidence indications of the subject in at least one database;

obtaining genetic information from each of a plurality of subjects in the at least one database;

operably connecting at least one extractor to the at least one database, wherein the extractor is configured to extract one or more features from the genetic and clinical information stored in the at least one database; and, operably connecting at least one treatment efficacy monitor to the at least one extractor, operably connecting at least one classifier to the extractor and to the recommender, wherein the classifier is configured to classify the one or more features extracted from the genetic and clinical information, and wherein classifier training comprises:

(a) providing a plurality of different classes, wherein each class represents a set of subjects with a shared characteristic;

(b) providing a multi-parametric model representative of the cfNAs from each of a plurality of samples belonging to each of the classes, thereby providing a training data set; and (c) training a learning algorithm on the training data set to create one or more trained classifiers, wherein each trained classifier comprises one or more random forests, linear classifiers, support vector machines, and/or Hidden Markov models (HMMs), and classifies a test sample into one or more of the plurality of classes, thereby generating the system;

wherein the at least one treatment efficacy monitor is configured to:

implement the one or more trained classifiers to determine treatment efficacy for at least one treatment from among a plurality of treatment options for a cancer of at least one test subject of the plurality of subjects, based at least in part on an analysis of the one or more features at a first time point of the two or more time points; and implement the one or more trained classifiers to determine an effective treatment from among a plurality of treatment options for a cancer of at least one test subject of the plurality of subjects, wherein selection of the treatment, based on at least an analysis of the:

one or more features comprising genetic information for the given subject from a second time point of the two or more time points; and amount of time between at least two or more time points.

2. The method of claim 1, wherein the plurality of subjects comprises subjects having cancer.

3. The method of claim 1, wherein the plurality of subjects comprises cancer-free subjects.

4. The method of claim 1, further comprising operably connecting at least one genetic analyzer to the system, wherein the genetic analyzer is configured to the genetic information.

5. The method of claim 1, further comprising operably connecting at least one report generator to the recommender.

6. The method of claim 1, wherein the genetic information comprises unstructured text data.

7. The method of claim 1, comprising storing the clinical information in at least one database array.

8. The method of claim 1, wherein the clinical information comprises patient information from physicians and test labs.

9. The method of claim 1, wherein the clinical information comprises CT scans, MRI scans, ultrasound scans, bone scans, PET scans, bone marrow tests, X-rays, endoscopies, lymphangiograms, intravenous urograms (IVU), IV pyelograms (IVP), lumbar punctures, cystoscopies, immunological tests, histology reports, and/or cancer marker tests.

10. The method of claim 1, further comprising using the system to predict a course of treatment for at least one test subject having cancer.

11. The system generated by the method of claim 1.

12. The method of claim 1, wherein the plurality of different classes is selected from the group consisting of: cancer-free, breast cancer, colon cancer, lung cancer, pancreatic cancer, prostate cancer, ovarian cancer, melanoma, and liver cancer.

13. The method of claim 1, wherein the one or more features comprise treatment responses to therapeutic interventions to generate one or more treatment classifications.

14. The method of claim 13, wherein the one or more treatment classifications comprise responsive to treatment, nonresponsive to treatment, or a level of responsiveness to treatment.

15. The method of claim 1, further comprising operably connecting at least one inference unit to the classifier and to the recommender.

16. The method of claim 15, wherein output of the classifier is provided to the inference unit.

17. The method of claim 1, wherein a diagnostic confidence indication can be increased in the subsequent characterization if the information from a first time point corroborates information from the second time point.

18. The method of claim 1, wherein diagnostic confidence indication can be decreased in the subsequent characterization if the information from a first time point conflicts with information from the second time point.

19. The method of claim 1, comprising detecting genetic variants in the noise range of a machine configured to generate the plurality of sequencing reads.

* * * * *